(12) United States Patent
Peyton

(10) Patent No.: US 8,613,707 B2
(45) Date of Patent: Dec. 24, 2013

(54) SYSTEM AND METHOD FOR MONITORING CARDIAC OUTPUT

(75) Inventor: Philip John Peyton, Park Orchards (AU)

(73) Assignee: Austin Health, Heidelberg (AU)

( * ) Notice: Subject to any disclaimer, the term of this patent is extended or adjusted under 35 U.S.C. 154(b) by 475 days.

(21) Appl. No.: 12/743,224

(22) PCT Filed: Nov. 14, 2008

(86) PCT No.: PCT/AU2008/001696
§ 371 (c)(1),
(2), (4) Date: Sep. 20, 2010

(87) PCT Pub. No.: WO2009/062255
PCT Pub. Date: May 22, 2009

(65) Prior Publication Data
US 2011/0004108 A1    Jan. 6, 2011

Related U.S. Application Data

(60) Provisional application No. 61/003,544, filed on Nov. 16, 2007.

(51) Int. Cl.
*A61B 5/02* (2006.01)
(52) U.S. Cl.
USPC ................ 600/504; 600/484; 600/532
(58) Field of Classification Search
USPC .............. 600/481, 483, 484, 504, 526, 532
See application file for complete search history.

(56) References Cited

U.S. PATENT DOCUMENTS

| | | | |
|---|---|---|---|
| 5,632,281 A | 5/1997 | Rayburn | 128/719 |
| 5,971,934 A | 10/1999 | Scherer et al. | 600/526 |
| 6,217,524 B1 | 4/2001 | Orr et al. | |

FOREIGN PATENT DOCUMENTS

| | | |
|---|---|---|
| JP | 5137789 | 6/1993 |
| WO | 00/42908 | 7/2000 |
| WO | 00/67634 | 11/2000 |
| WO | 2006/119546 | 11/2006 |
| WO | 2008/014788 | 2/2008 |

OTHER PUBLICATIONS

Peyton et al., "Noninvasive, Automated and Continuous Cardiac Output Monitoring by Pulmonary Capnodynamics. Breath-by-breath Comparison with Ultrasonic Flow Probe," *Anesthesiology*, 105 (1): 72-80, 2006.
International Search Report, mailed Feb. 18, 2009, for PCT/AU2008/001696, 3 pages.
Written Opinion of the International Searching Authority, mailed Feb. 18, 2009, for PCT/AU2008/001696, 6 pages.

(Continued)

*Primary Examiner* — Navin Natnithithadha
*Assistant Examiner* — Etsub Berhanu
(74) *Attorney, Agent, or Firm* — Seed IP Law Group PLLC

(57) ABSTRACT

A method for monitoring cardiac output (pulmonary blood flow) of a subject, the method including: measuring a first net pulmonary uptake or elimination of a breathed gas species by the subject and a first partial pressure of the gas species at a first time, and at a second time later than the first time, determining a first pulmonary blood flow of the patient at the first time, and determining a pulmonary blood flow of the subject at the second time on the basis of the first pulmonary blood flow, the first net pulmonary uptake or elimination, the second net pulmonary uptake or elimination, the first partial pressure, and the second partial pressure.

23 Claims, 11 Drawing Sheets

(56) References Cited

OTHER PUBLICATIONS

Brudin L.H., Rhodes C.G., Valind S.O., Jones T., Jonson B. and Hughes J.M.B. "Relationships between regional ventilation and vascular and extravascular volume in supine humans," *J Appl Physiol.* 1994; 76(3): 1195-1204.

Cander L., Forster R.E. "Determination of pulmonary parenchymal tissue volume and pulmonary capillary blood flow in man," *J Appl Physiol.* 1959; 14(4): 541-551.

Capek J. M., Roy R.J. "Noninvasive Measurement of Cardiac Output During Partial CO2 Rebreathing," *IEEE Transactions on Biomedical Engineering.* 1988; 35(9): 653-61.

Capek J. M., Roy R.J. "Encyclopedia of Medical Devices and Instrumentation.," J.G. Webster Ed., Wiley, N.Y., 1988, pp. 1309-1310.

Defares J.G. "Determination of PvCO2 From the exponential CO2 Rise During Rebreathing," *J Appl Physiol.* 1958; 13(2): 159-64.

Gabrielsen A., Videbaek R., Schou M., Damgaard M., Kastrup J., Norsk P. "Non-invasive measurement of cardiac output in heart failure patients using a new foreign gas rebreathing technique," *Clinical Science.* 2002; 102(2): 247-52.

Gedeon A., Forslund L., Hedenstierna G. and Romano E. "A new method for non-invasive bedside determination of pulmonary blood flow," *Med Biol Eng Comput.* 1980; 18(4): 411-8.

Hook C., Meyer M. "Pulmonary blood flow, diffusing capacity and tissue volume by rebreathing: theory," *Respir Physiol.* 1982; 48(2): 255-279.

Kim T.S., Rahn H., Farhi L.E. "Estimation of true venous and arterial PCO2 by gas analysis of a single breath," *J Appl Physiol.* 1966; 21(4): 1338-44.

McDonnell W.F. and Seal E. "Relationships between lung function and physical characteristics in young adult black and white males and females," *Eur respir J.* 1991; 4(3): 279-89.

Petrini M.F., Peterson B.T., Hyde R.W. "Lung tissue volume and blood flow by rebreathing: theory," *J Appl. Physiol.* 1978; 44(5): 795-802.

Peyton P.J., Robinson G.J.B., McCall P.R. and Thompson B. "Non-invasive measurement of intrapulmonary shunting," *J Cardiothoracic Vasc Anesth.* 2004; 18(1): 47-52.

Robinson G.J.B., Peyton P.J., Vartuli G.M., Burfoot R.B., Junor P.A. "Continuous Measurement of Cardiac Output by Inert Gas Throughflow —Comparison with Thermodilution," *J. Cardiothoracic Vasc Anesth.* 2003; 17(2): 204-10.

Russell A.E., Smith S.A., West M.J., Aylward P.E., McRitchie R.J., Hassam R.M., Minson R.B., Wing L.M.H. and Chalmers J.P. "Automated non-invasive measurement of cardiac output by the carbon dioxide rebreathing method: comparisons with dye dilution and thermodilution," *Br Heart J.* 1990; 63(3): 195-9.

Sackner M.A., Khalil A.F. and DuBois A.B. "Determination of tissue volume and carbon ioxide dissociation slope of the lungs in man," *J Appl Physiol.* 1964; 19(3): 374-80.

Yem J.S., Tang Y., Turner M.J. and Baker A.B. "Sources of Error in Noninvasive Pulmonary Blood Flow Measurements by Partial Rebreathing," *Anesthesiology* 2003; 98(4): 881-7.

SYSTEM AND METHOD FOR MONITORING CARDIAC OUTPUT

FIELD

The present invention relates to a method and system for monitoring the cardiac output of a subject, in particular for non-invasively determining cardiac output with each breath of the subject so that it can be monitored in a substantially continuous manner.

BACKGROUND

Cardiac output (pulmonary blood flow) is the rate at which blood is pumped by the heart to the body. Along with the blood pressure, it fundamentally reflects the degree of cardiovascular stability and the adequacy of perfusion of vital organs. Knowledge of the cardiac output will not itself provide a diagnosis of a patient's condition, but can provide information useful in making a diagnosis. Monitoring cardiac output is most important where cardiovascular instability is threatened, such as during major surgery and in critically ill patients. In these situations "moment to moment" or continuous monitoring is most desirable, since sudden fluctuations and rapid deterioration can occur, for instance, where sudden blood loss complicates an operation.

Continuous monitoring of cardiac output is still not performed routinely during anaesthesia and critical care due to the absence of a convenient, safe, non-invasive and accurate method. The established techniques for measuring cardiac output, such as pulmonary thermodilution via a pulmonary artery catheter, are invasive and associated with occasional but serious complications, such as pulmonary artery rupture, and/or are time consuming and heavily operator dependent, as in the case of Doppler echocardiography. Other indicator dilution techniques are available, but are invasive and poorly adapted to routine clinical monitoring requirements. Improvements in this field are taking place, such as the development of pulse contour techniques, transpulmonary thermodilution, and improved thoracic bioimpedance devices, but these all have limitations, such as poor accuracy under clinical conditions, the need for repeated calibration, invasive central or peripheral cannulation, and/or are simply unsuitable for patients during surgery and critical care who are intubated or ventilated.

Techniques based on pulmonary gas exchange measurement are among the oldest methods used for cardiac output measurement, and are attractive because of their potentially non-invasive nature. Recent refinements have produced systems or devices based on inert gas uptake (Innocor, Innovision, Denmark), partial $CO_2$ rebreathing (NICO, Respironics, USA) and differential lung ventilation via a double lumen endobronchial tube (the throughflow method). (Gabrielsen et al 2002, Capek and Roy 1988, Robinson et al 2003). However, none of these alternatives allows truly continuous and non-invasive cardiac output monitoring. It follows that it would be useful to provide an automated, non-invasive, continuous measurement method and system suitable for routine use in patients undergoing general anaesthesia or in intensive care.

Non-shunt ("effective") pulmonary capillary blood flow $\dot{Q}c$ is that part of the total pulmonary blood flow (cardiac output, $\dot{Q}t$) which engages in gas exchange with an inspired gas mixture in the lung.

The Fick equation, based on the principle of conservation of mass, when applied to elimination of carbon dioxide ($CO_2$) by the lungs, states that $$\dot{Q}t(Ca_{CO_2} - C\bar{v}_{CO_2}) = \dot{V}_{CO_2} \qquad \text{Equation (1)}$$

where $\dot{V}_{CO_2}$ is the rate of uptake or elimination of $CO_2$ by the lungs, and $C\bar{v}_{CO_2}$ and $Ca_{CO_2}$ respectively are the (dimensionless) contents of $CO_2$ in mixed venous blood and arterial blood.

$\dot{Q}c$ can be related to measured $\dot{V}_{CO_2}$ by a variation of the Fick equation:

$$\dot{Q}c = \frac{\dot{V}_{CO_2}}{(Cc'_{CO_2} - C\bar{v}_{CO_2})}. \qquad \text{Equation (2)}$$

where $Cc'_{CO_2}$ and $C\bar{v}_{CO_2}$ are the fractional contents of $CO_2$ in pulmonary end-capillary and mixed venous blood, respectively. Since the pulmonary end-capillary blood and alveolar gas can be considered to be in equilibrium with one another, $Cc'_{CO_2}$ can be related to the content of $CO_2$ in the alveolar gas mixture if the solubility of $CO_2$ in blood is known, so that $$\dot{Q}c = \frac{\dot{V}_{CO_2}}{\left(S_{CO_2} \cdot \frac{P_{A_{CO_2}}}{P_B} - C\bar{v}_{CO_2}\right)} \qquad \text{Equation (3)}$$

where $P_{A_{CO_2}}$ is the alveolar partial pressure of $CO_2$, and $P_B$ is the atmospheric pressure corrected for the presence of water vapour at body temperature (47 mmHg at 37° C.). $S_{CO_2}$ is the blood-gas partition coefficient of $CO_2$, a constant representing the solubility of $CO_2$ in blood under the conditions present in the patient at that time.

To permit non-invasive measurement, measured partial pressure of $CO_2$ in end-tidal gas ($P_{E'_{CO_2}}$) is used as an approximation of $P_{A_{CO_2}}$ so that Equation (3) can be rewritten as:

$$\dot{Q}c = \frac{\dot{V}_{CO_2}}{\left(S_{CO_2} \cdot \frac{P_{E'_{CO_2}}}{P_B} - C\bar{v}_{CO_2}\right)} \qquad \text{Equation (4)}$$

$\dot{Q}c$ can be determined non-invasively by application of the differential Fick principle (Capek and Roy, 1988). This combines two simultaneous versions of Equation (4) where $\dot{Q}c$ and $C\bar{v}_{CO_2}$ are assumed to be constant, as follows:

$$\dot{Q}c = \frac{\dot{V}_{CO_{2i}} - \dot{V}_{CO_{2j}}}{\frac{S_{CO_2}}{P_B} \cdot \left(P_{E'_{CO_{2i}}} - P_{E'_{CO_{2j}}}\right)} \qquad \text{Equation (5)}$$

The variables in this equation are measured at two points in time (i and j), before and after inducing a change in the alveolar minute ventilation, which alters both $\dot{V}_{CO_2}$ and $P_{E'_{CO_2}}$ acutely. This can be achieved by a number of means. The first method used in the past is to make a stepwise change in the respiratory rate (Gedeon et al 1980). An alternative method, referred to as partial $CO_2$ rebreathing, is to introduce a change in the serial deadspace, while holding tidal volume constant, thereby effectively reducing the alveolar ventilation (Capek and Roy, 1988). This is the technique used by the NICO device (Respironics, USA). This approach obviates the need to know the mixed venous $CO_2$ content ($C\bar{v}_{CO_2}$), which could otherwise only be directly measured by invasive mixed venous blood sampling via a pulmonary artery catheter. $\dot{Q}c$ requires correction using an estimate of pulmonary shunt fraction ($\dot{Q}s/\dot{Q}t$). This estimate can be obtained by a number of means, including non-invasively (Peyton et al 2004). This then permits the determination of total pulmonary blood flow (cardiac output, $\dot{Q}t$), as follows:

$$\dot{Q}t = \frac{\dot{Q}c}{1 - \frac{\dot{Q}s}{\dot{Q}t}} \qquad \text{Equation (6)}$$

The acute change in $\dot{V}_{CO_2}$ and $P_{E'CO_2}$ rapidly levels out as washin or washout of $CO_2$ from alveolar gas and lung tissue stores briefly approaches a new steady state level (Gedeon et al 1980, Capek and Roy, 1988). However, the change in alveolar ventilation begins to alter the content of $CO_2$ in the mixed venous blood, Importantly, stability in both $C\bar{v}_{CO_2}$ and $\dot{Q}c$ is required for equation (6) to be accurate, and the measurement cannot be repeated more frequently than once every 3-4 minutes to allow $C\bar{v}_{CO_2}$ to stabilise prior to the next measurement. For this reason it has not been previously possible to provide accurate continuous (breath-by-breath) monitoring of cardiac output.

Orr et al (U.S. Pat. No. 6,217,524 B1) have described an approach to the provision of continuous (breath to breath) monitoring of cardiac output, by the ongoing measurement of $\dot{V}_{CO_2}$ with each breath, following an initial baseline measurement of cardiac output and $\dot{V}_{CO_2}$. Their approach makes the assumption, based on the well-known fact that $CO_2$ stores in the body are very large, that the arterio-venous $CO_2$ content difference ($Ca_{CO_2} - C\bar{v}_{CO_2}$) will remain constant for some time following a change in cardiac output. From this assumption, it follows that, if $\dot{Q}t$ at a breath i ($\dot{Q}t_i$) changes on a subsequent breath k to $\dot{Q}t_k$, then $\dot{Q}t_k$ can be derived from two simultaneous versions of equation (1), in which the arterio-venous $CO_2$ content difference ($Ca_{CO_2} - C\bar{v}_{CO_2}$) cancels out, giving $$\dot{Q}t_k = F \cdot \dot{V}_{CO_{2k}} \qquad \text{Equation (7a)}$$

where $\dot{V}_{CO_{2k}}$ is $\dot{V}_{CO_2}$ at breath k, and F is a scaling factor given by $$F = \frac{\dot{Q}t_i}{\dot{V}_{CO_{2i}}} \qquad \text{Equation (7b)}$$

where $\dot{V}_{CO_{2i}}$ is $\dot{V}_{CO_2}$ measured at breath i. This method determines an estimate of cardiac output on a breath-by-breath basis from a previous measurement of $CO_2$ elimination by the lungs and a previous measurement of cardiac output, such as might be obtained from equation (5) above.

However, experimental testing of the Orr et al method by the inventor has found it to be unacceptably inaccurate. Continuous breath-by-breath estimations of cardiac output made using the Orr method were compared on a breath by breath basis with simultaneous measurements made by a "gold standard" in vivo measurement device, an indwelling ultrasonic flow probe placed on the ascending aorta or pulmonary artery in six ventilated sheep ranging in weight from 35-45 kg. The sheep were anaesthetised with isoflurane in oxygen-air, and their cardiac output was manipulated using a dobutamine infusion alternating with esmolol boluses. $\dot{V}_{CO_2}$ was measured at the mouth with each breath using a calibrated measurement system incorporating a pneumotachograph and sidestream rapid gas analyser. A single initial calibration cardiac output was measured by introducing a step change in tidal volume for 30 seconds and applying equation (5). Cardiac output was then followed breath-by-breath for up to 100 minutes. The results are shown in FIGS. 7 and 9.

Overall mean bias for $\dot{Q}t$ (Orr et al—flow probe) was −0.34 L/min [95% confidence limits: ±0.04 L/min]. The standard deviation of the difference was 1.16 L/min, giving upper and lower limits of agreement of +1.9 and −2.6 L/min Intraclass correlation coefficients (ICC) over successive 5 minute intervals were 0.65 for agreement in $\dot{Q}t$, and 0.55 for agreement in changes in $\dot{Q}t$. From this it can be determined that only approximately 30-40% of the actual variation in cardiac output measured by the flow probe was reflected in the corresponding changes estimated by the method of Orr et al. This level of agreement with the gold standard was not improved by nominating the $\dot{Q}t$ measured by the flow probe at the initial calibration point as $\dot{Q}t_i$.

The method described by Orr et al produces an overdamped or "flat" response to real changes in $\dot{Q}t$. The origins of this flat responsiveness lie in the assumption underlying the method of Orr et al that the arterio-venous $CO_2$ content difference is unaffected in the short term by changes in $\dot{Q}t$. This assumption implies a simple linear relationship between changes in $\dot{Q}t$ and changes in $\dot{V}_{CO_2}$, which is not borne out by the experimental data shown in FIG. 7.

The consequence of Orr et al's assumption is a tendency to "normalise" the estimated cardiac output toward the initial baseline measurement, despite significant actual changes in $\dot{Q}t$. The clinical consequences of this are potentially serious, where the magnitude of a sudden deterioration in a patient's condition during anaesthesia for surgery, or in critical care, is underestimated, potentially resulting in an inadequate response by treating clinicians.

It is desired, therefore, to provide a method and system for monitoring cardiac output of a subject that alleviate one or more difficulties of the prior art, or at least to provide a useful alternative.

SUMMARY

In one aspect, the present invention provides a method for monitoring cardiac output of a subject, the method including:
(i) measuring a first net pulmonary uptake or elimination of a breathed gas species by said subject at a first time;
(ii) measuring a first partial pressure of said gas species in lungs of said subject at said first time;
(iii) determining a first pulmonary blood flow of said patient at said first time;
(iv) measuring a second net pulmonary uptake or elimination of said breathed gas species by said subject at a second time later than said first time;
(v) measuring a second partial pressure of said gas species in lungs of said subject at said second time; and
(vi) determining a pulmonary blood flow of said subject at said second time on the basis of said first pulmonary blood flow, said first net pulmonary uptake or elimination, said second net pulmonary uptake or elimination, said first partial pressure, and said second partial pressure.

Preferably, the method includes measuring said net rates of pulmonary uptake or elimination of said gas species G at respective breaths of said subject.

Preferably, the method includes performing said step of determining at successive breaths of said subject to provide breath-by-breath monitoring of said cardiac output of said subject.

The present invention also provides a method for monitoring cardiac output (pulmonary blood flow) of a subject, including:

determining pulmonary blood flow $\dot{Q}t_k$ for a breath k of said subject according to:

$$\dot{Q}t_k = \dot{Q}t_i \cdot \left(\frac{\dot{V}_{G_k}}{\dot{V}_{G_i}}\right)^2$$

where $\dot{V}_{G_i}$ and $\dot{V}_{G_k}$ are net rates of pulmonary uptake or elimination of a gas species G for breath k and for an earlier breath i, respectively, and $\dot{Q}t_i$ is a pulmonary blood flow of said subject for said breath i.

Advantageously, the method may be executed by a computer system having means for receiving gas partial pressure and gas flow data representing constituents, partial pressures and flow rates of a gas species inhaled and exhaled by said subject at said first time and said earlier time; and means for processing said gas species data to determine said cardiac output of said subject at said subsequent time.

The present invention also provides a method for monitoring cardiac output of a subject, including:

determining pulmonary blood flow $\dot{Q}t_k$ for a breath k of said subject according to:

$$\dot{Q}t_k = \dot{Q}t_i \cdot \left(\frac{\dot{V}_{G_k}}{\dot{V}_{G_i}}\right)^2 \cdot \text{corr}$$

where $\dot{V}_{G_i}$ and $\dot{V}_{G_k}$ are net rates of pulmonary uptake or elimination of a gas species G for said breath k and for an earlier breath i, respectively, $\dot{Q}t_i$ is a pulmonary blood flow of said subject for said breath i, and corr represents at least one correction factor to correct the measured value of at least one of $\dot{V}_{G_i}$ and $\dot{V}_{G_k}$.

The present invention also provides a system for monitoring cardiac output of a subject having components for executing the steps of any one of the above processes.

The present invention also provides a computer-readable storage medium having stored thereon program instructions for executing the steps of any one of the above processes.

The present invention also provides a system for monitoring cardiac output of a subject, including:

means for receiving gas species partial pressure and flow data representing constituents, partial pressures and flow rates of gas inhaled and exhaled by said subject at one or more subsequent times and an earlier time; and means for processing said gas species partial pressure and flow data to determine a pulmonary blood flow of said subject at said one or more subsequent times based on a pulmonary blood flow of said subject at said earlier time and said constituents, partial pressures and flow rates of gas.

Advantageously, the system may further include a gas analyser for receiving and measuring the partial pressure of gas breathed by said subject; and a gas flow device for determining flow of said gas breathed by said subject.

Advantageously, said subject may be a human being.

Preferably, said gas species includes $CO_2$.

The gas species G can be an inert gas species administered to the patient by inhalation or otherwise. Alternatively, the gas species G can be a physiological respired gas species, preferably carbon dioxide ($CO_2$). For convenience, embodiments of the invention are hereinafter described with reference to the use of $CO_2$ as the gas G. However it is to be understood that other physiological gas species can also be used.

Preferably, the method includes the use of a data averaging or smoothing function to determine the $\dot{Q}t$ of the subject.

The present invention also provides a system for monitoring cardiac output (pulmonary blood flow) of a subject, the system including means for:

(i) measuring a first net pulmonary uptake or elimination of a breathed gas species by said subject at a first time;
(ii) measuring a first partial pressure of said gas species in lungs of said subject at said first time;
(iii) determining a first pulmonary blood flow of said patient at said first time;
(iv) measuring a second net pulmonary uptake or elimination of said breathed gas species by said subject at a second time later than said first time;
(v) measuring a second partial pressure of said gas species in lungs of said subject at said second time; and
(vi) determining a pulmonary blood flow of said subject at said second time on the basis of said first pulmonary blood flow, said first net pulmonary uptake or elimination, said second net pulmonary uptake or elimination, said first partial pressure, and said second partial pressure.

Preferably, the system includes:

one or more breathing systems for ventilating lungs of the subject;
a rapid gas analyser and gas flow measuring device to allow measurement of alveolar (end-tidal) partial pressure and pulmonary uptake or elimination of a gas species G;
a data processor with inputs to receive data from the rapid gas analyser and gas flow measuring device, said processor being configured to determine or register $\dot{Q}t$ and $\dot{V}_{G_i}$ data received relating to a breath i
a means for measuring patient temperature and blood gas, acid base and hemoglobin concentration, to provide one or more corrections to measured $\dot{V}_{G_i}$ and $\dot{V}_{G_k}$
and wherein the processor is further configured to use the value of $\dot{Q}t$ and $\dot{V}_{G_i}$ data received relating to a breath i and $\dot{V}_{G_k}$ data received relating to a breath k, to determine the cardiac output for breath k ($\dot{Q}t_k$), and means for communicating to an operator of the system at least an indication of the cardiac output for breath k.

Advantageously, said means may include one or more visual or audio display device(s).

The system may have other components and the processor may have other functions to assist in the breath by breath measurement of cardiac output. For example, the processor may also have input means for inputting the haemoglobin content of the subject and the processor may also have an input for receiving data from a device for measuring arterial oxygen content, such as a pulse oximeter, and/or for measuring pH and/or arterial $CO_2$ partial pressure. These would be of assistance in allowing the processor to determine the shunt fraction of pulmonary blood flow using standard methods, thereby allowing the processor to allow concurrent monitoring of the patient's metabolic, acid-base status and lung function and tissue oxygenation.

The system preferably automatically displays and records relevant data in real time.

The present invention also provides a computer-readable storage medium having stored therein programming instructions for executing the steps of:

(i) accessing first gas species data representing a first net pulmonary uptake or elimination of a breathed gas species by said subject at a first time, and a first partial pressure of said gas species in lungs of said subject at said first time;

(ii) determining a first pulmonary blood flow of said patient at said first time;

(iii) accessing second gas species data representing a second net pulmonary uptake or elimination of said breathed gas species by said subject at a second time later than said first time, and a second partial pressure of said gas species in lungs of said subject at said second time; and (iv) processing said first gas species data and said second gas species data to determine a pulmonary blood flow of said subject at said second time on the basis of said first pulmonary blood flow, said first net pulmonary uptake or elimination, said second net pulmonary uptake or elimination, said first partial pressure, and said second partial pressure.

Preferred embodiments of the present invention allow the cardiac output ($\dot{Q}t$) measured or otherwise determined for a given breath "i" ($\dot{Q}t_i$) to be used to accurately determine $\dot{Q}t$ of a subsequent breath "k" ($\dot{Q}t_k$). This permits continuous, ongoing, breath-by-breath monitoring of $\dot{Q}t$, and in particular the effectively immediate identification of acute changes in $\dot{Q}t$.

BRIEF DESCRIPTION OF THE DRAWINGS

Preferred embodiments of the invention are hereinafter described, by way of example only, with reference to the accompanying drawings, in which.

DETAILED DESCRIPTION OF THE PREFERRED EMBODIMENTS

Figure 1:
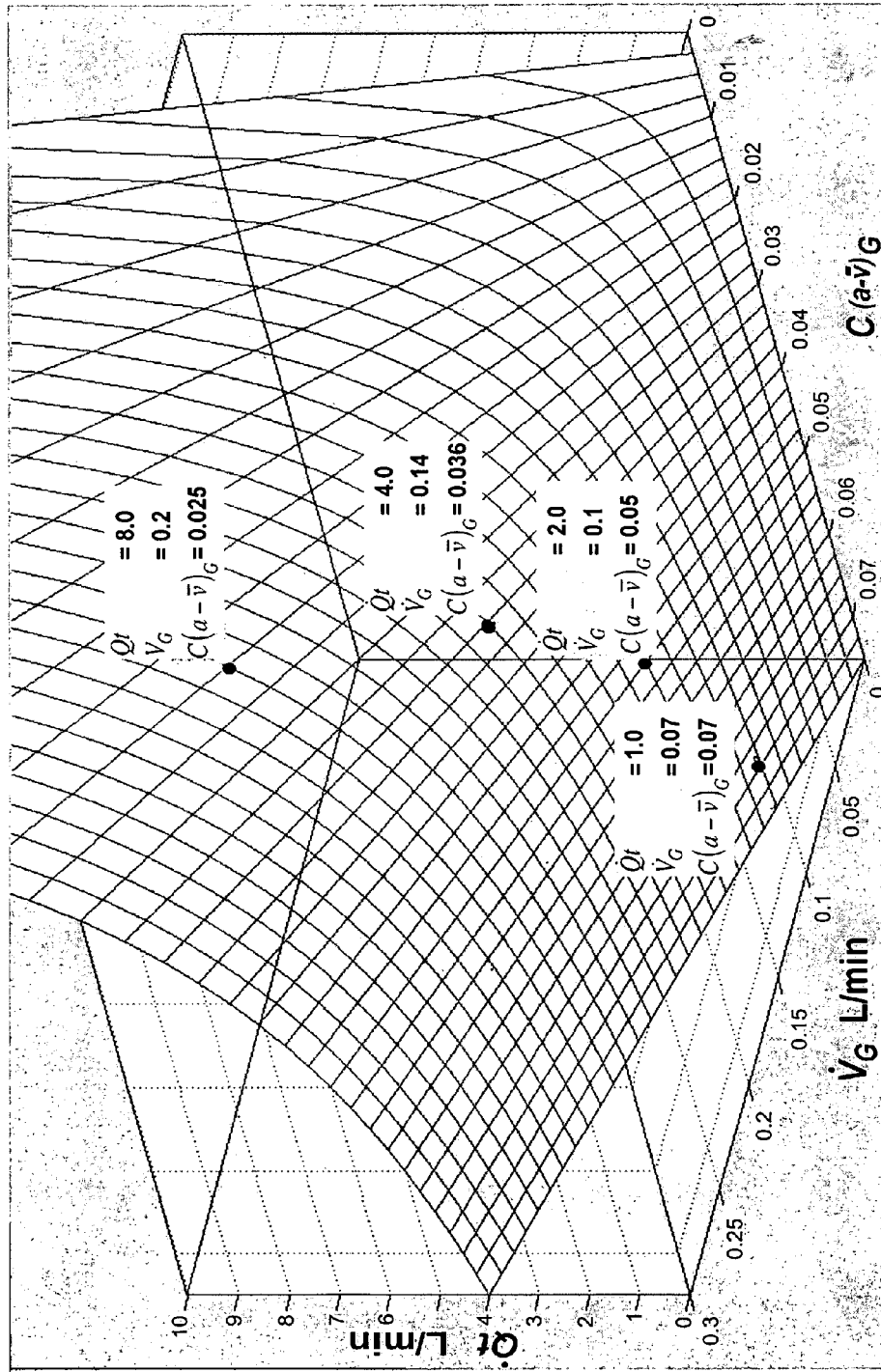
FIG. 1 is a graphical representation of the relationships between the three physiological variables $\dot{V}_G$, the net rate of uptake or elimination of G by the lungs, $C(a-\bar{v})_G$, the arterio-venous content difference of G in blood; and $\dot{Q}t$, the cardiac output, where G is carbon dioxide.

A method for monitoring cardiac output (pulmonary blood flow, $\dot{Q}t$), preferably in an automated and breath-by-breath manner, is also referred to herein as "the capnotracking method". It is non-invasive and is suitable for use in patients during anaesthesia or in critical care who are intubated with either an endotracheal tube, endobronchial tube, or laryngeal mask airway or similar airway management device.

The method is based on the uptake or elimination of carbon dioxide ($CO_2$) and/or other gases by the lungs. The prefix capno used in this specification refers to use of measurement of $CO_2$ to determine cardiac output. $CO_2$ is the preferred gas to measure, since it is present under all physiological conditions. However, other breathed gases, such as anaesthetic gases being administered to the patient, can be used instead, or at the same time. Consequently, the use of the prefix capno should not be understood as limiting the invention to the use of $CO_2$.

With every breath, the rate of elimination of $CO_2$ by the lungs, and preferably also the partial pressure of $CO_2$ in gas expired from the lungs at the end of a breath, the end-expired partial pressure (referred to as end-tidal partial pressure), is measured in real time. The method can achieve continuous measurement of cardiac output by the application, with each of a plurality of successive breaths, of a "continuity equation" as described below. This determines a change in cardiac output relative to a baseline measurement of cardiac output from the measured inputs. In contrast to the method of Orr et al., no a priori assumption is made regarding the stability or movement of the arterio-venous $CO_2$ content difference.

The baseline cardiac output measurement can be obtained by any one of a number of methods, including those described herein, but the preferred means is by application of the "calibration equation" of equation (5). This uses the same inputs as the continuity equation, but the inputs are measured immediately before and after the level of alveolar ventilation of the lungs is changed.

The theoretical basis and derivation of the continuity equation is described below.

The following description applies to any gas species "G" present in the alveolar gas mixture. To explain the concepts, a simplified model of the lung is used, wherein the lung is considered to be a single compartment consisting of alveolar gas and lung tissue and pulmonary capillary blood in equilibrium with one another. A gas species G enters the lung compartment in inspired gas and mixed venous blood, and leaves it in expired alveolar gas, and as arterial blood. The content of G in mixed venous blood and arterial blood is $C\bar{v}_G$ and $Ca_G$ respectively.

The Fick equation, based on the principle of conservation of mass, for a gas G, states that $$\dot{Q}t(Ca_G - C\bar{v}_G) = \dot{V}_G \qquad \text{Equation (8)}$$

where $\dot{V}_G$ is the rate of uptake or elimination of G by the lungs.

Considering the arterio-venous content difference of G as a single variable $(C(a-\bar{v})_G)$, we have an equation:

$$\dot{Q}t(C(a-\bar{v})_G) = \dot{V}_G \qquad \text{Equation (9)}$$

with two unknowns, $C(a-\bar{v})_G$ and $\dot{Q}t$.

Equation (9) for two breaths i and k can be combined $$\frac{\dot{Q}t_k \cdot C(a-\bar{v})_{G_k}}{\dot{Q}t_i \cdot C(a-\bar{v})_{G_i}} = \frac{\dot{V}_{G_k}}{\dot{V}_{G_i}} \qquad \text{Equation (10)}$$

and transposed, so that, $$\dot{Q}t_k = \dot{Q}t_i \cdot \frac{\dot{V}_{G_k}}{\dot{V}_{G_i}} \cdot \frac{C(a-\bar{v})_{G_i}}{C(a-\bar{v})_{G_k}} \qquad \text{Equation (11)}$$

Determination of the Relationship of the Variables in the Fick Equation:

While $\dot{V}_G$, the net rate of uptake or elimination of G by the lungs, can be measured non-invasively, Equation (9) has two unknowns, $C(a-\bar{v})_G$ and $\dot{Q}t$. The relationship of these three variables can be displayed graphically using a 3-dimensional surface plot, with $\dot{Q}t$ as the vertical axis, as shown in FIG. 1. The units chosen are typical values over a physiologically relevant range, where G is carbon dioxide, the preferred gas with which to make the measurements.

For the purposes of the analysis, $\dot{Q}t$ is the independent variable. Movement in $\dot{V}_G$ and $C(a-\bar{v})_G$ in response to a change in $\dot{Q}t$ follows a path simultaneously described by two vectors in the planes $\dot{V}_G$-$\dot{Q}t$ and $C(a-\bar{v})_G$-$\dot{Q}t$. These are respectively described by the partial derivatives of $\dot{V}_G$ and $C(a-\bar{v})_G$ with respect to $\dot{Q}t$:

$$\frac{\partial \dot{V}_G}{\partial \dot{Q}t} = C(a-\bar{v})_G = \frac{\dot{V}_G}{\dot{Q}t} \qquad \text{Equation (12)}$$

and $$\frac{\partial C(a-\bar{v})_G}{\partial \dot{Q}t} = -\frac{\dot{V}_G}{\dot{Q}t^2} = \frac{C(a-\bar{v})_G}{\dot{Q}t} \qquad \text{Equation (13)}$$

From this, the relationships between the changes in $C(a-\bar{v})_G$ and $\dot{V}_G$, respectively, in response to a change in $\dot{Q}t$, are given by $$\frac{\partial \dot{V}_G}{\dot{V}_G} = \frac{\partial \dot{Q}t}{\dot{Q}t} \qquad \text{Equations (14a) and (14b)}$$

and $$-\frac{\partial C(a-\bar{v})_G}{C(a-\bar{v})_G} = \frac{\partial \dot{Q}t}{\dot{Q}t}$$

Transposing and integrating both sides gives:

$$\log\left(\frac{\dot{V}_G}{\dot{Q}t}\right) = m \qquad \text{Equations (15a) and (15b)}$$

and $$\log(C(a-\bar{v})_G \cdot \dot{Q}t) = n$$

where m and n are respective constants of integration.

For a given breath i and a subsequent breath k:

$$\log\left(\frac{\dot{V}_{G_i}}{\dot{Q}t_i}\right) = \log\left(\frac{\dot{V}_{G_k}}{\dot{Q}t_k}\right) \qquad \text{Equation (16a)}$$

and $$\log(C(a-\bar{v})_{G_i} \cdot \dot{Q}t_i) = \log(C(a-\bar{v})_{G_k} \cdot \dot{Q}t_k) \qquad \text{Equation (16b)}$$

Taking antilogs and transposing yields $$\frac{\dot{V}_{G_k}}{\dot{V}_{G_i}} = \frac{\dot{Q}t_k}{\dot{Q}t_i} \text{ and } \frac{C(a-\bar{v})_{G_i}}{C(a-\bar{v})_{G_k}} = \frac{\dot{Q}t_k}{\dot{Q}t_i} \qquad \text{Equation (17a) and (17b)}$$

This indicates that, in response to a change in $\dot{Q}t$ occurring, $C(a-\bar{v})_G$ and $\dot{V}_G$ will change and in opposite directions to each other, according to $$\frac{C(a-\bar{v})_{G_i}}{C(a-\bar{v})_{G_k}} = \frac{\dot{V}_{G_k}}{\dot{V}_{G_i}} \qquad \text{Equation (18)}$$

Combining Equation (11) with Equation (18) gives $$\dot{Q}t_k = \dot{Q}t_i \cdot \left(\frac{\dot{V}_{G_k}}{\dot{V}_{G_i}}\right)^2 \qquad \text{Equation (19)}$$

Equation 19 is referred to herein as the continuity equation, and it allows determination of an accurate estimate of $\dot{Q}t$ for any breath k following a measurement of $\dot{Q}t$ and $\dot{V}_G$ at a previous breath i.

The path described by this relationship is shown as solid black circles in FIG. 1, for a scenario in which $\dot{Q}t$ declines from 8 L/min to 4 L/min, 2 L/min, and 1 L/min. The arterio-venous content difference $C(a-\bar{v})_G$ is expected to more than double during this process.

Where alveolar ventilation can be assumed to remain substantially unchanged over a given period of time, changes in $\dot{V}_G$ will be closely reflected by corresponding changes in the measured difference between the inspired partial pressure of G($PI_G$) and its partial pressure in end-tidal gas ($PE'_G$). Substitution in Equation (19) can then be made according to $$\frac{\dot{V}_{G_k}}{\dot{V}_{G_i}} = \frac{PI_{G_k} - PE'_{G_k}}{PI_{G_i} - PE'_{G_i}} \qquad \text{Equation (20)}$$

This modified continuity equation allows a simplified measurement technique, as $PI_G$ and $PE'_G$ can be measured for a given breath by a standard clinical gas monitoring system, without the additional instrumentation and data processing required for direct measurement of $\dot{V}_G$.

Use of $CO_2$ as the Measurement Gas G

As described above, $CO_2$ is the preferred gas to measure, since it is present under all physiological conditions, and administration of the gas to the patient is not required. For this reason, the method is referred to as the "capnotracking" method (the prefix capno refers to $CO_2$) in the described embodiment, although other expired gases can be used instead, or as well.

Therefore, for $CO_2$:

$$\dot{Q}t_k = \dot{Q}t_i \left(\frac{\dot{V}_{CO_{2k}}}{\dot{V}_{CO_{2i}}}\right)^2 \qquad \text{Equation (21)}$$

$CO_2$ stores in the body are very large (over 100 liters), so that a change in $\dot{V}_{CO_2}$ in response to a sustained change in $\dot{Q}t$ will itself be sustained, maintaining the validity of equation (21) for a considerable period of time, as confirmed by experimental data.

Where alveolar ventilation can be assumed to remain substantially unchanged over a given period of time, changes in $\dot{V}_{CO_2}$ will be closely reflected by corresponding changes in the measured partial pressure of $CO_2$ in end-tidal gas ($PE'_{CO_2}$), assuming that inspired $CO_2$ partial pressure ($PI_{CO_2}$) is negligible or zero. Equation (21) can then be substituted according to $$\frac{\dot{V}_{CO_{2k}}}{\dot{V}_{CO_{2i}}} = \frac{PE'_{CO_{2k}}}{PE'_{CO_{2i}}} \qquad \text{Equation (22)}$$

This similarly allows a simplified measurement technique, as $PE'_{CO_2}$ can be measured for a given breath from a standard clinical monitoring capnography tracing, without the additional instrumentation and data processing required for measurement of $\dot{V}_{CO_2}$.

The method described above will accurately follow changes in $\dot{Q}t$ only where other factors do not influence the measured value of $\dot{V}_G$. Examples of such factors include changes in the metabolic rate of production or consumption of G, or the rate of its absorption or consumption by body tissues. Correction for this, for the respiratory gases $CO_2$ and $O_2$, can be made by measuring an index of metabolic rate, such as body temperature, and multiplying $\dot{V}_{G_k}$ by an appropriate correction factor. For example, metabolic rate can be assumed to reduce by approximately 7% for every 1° C. fall in body temperature, so $\dot{V}_{CO_{2k}}$ should be multiplied by $$(100 - 7\partial T)/100 \qquad \text{Equation (23)}$$

where $\partial T$ is the measured temperature difference between the patient's body temperature at breath k and at breath i.

The Use of Other Gases

Any gas that is administered to the patient other than via inhalation, such as by intravascular injection for example, should obey Equation (21).

Improved accuracy in the determination of $\dot{Q}t$ can also result from simultaneous measurement of the parameters described above for two or more gases present in the inspired or expired gas mixtures, and these measured parameters used to evaluate Equations (19) and/or (21). For example, $\dot{Q}t$ can be determined from the measured uptake of one or more inert anaesthetic gases G and simultaneously determined from the measured elimination of $CO_2$. It is also possible to use oxygen ($O_2$) as the measurement gas G, because $O_2$ uptake ($\dot{V}_{O_2}$) can be measured as described above in a similar manner to any other inspired gas. However, it should be noted that the use of $O_2$ presents greater difficulties for the determination of $\dot{Q}t$ by these equations because $O_2$ stores in the body are small due to its low solubility. Changes in $\dot{V}_{O_2}$ occurring in response to a sustained change in $\dot{Q}t$ will tend to return toward their baseline level, since $\dot{V}_{O_2}$ at a given time will be largely determined by the rate of metabolic $O_2$ production.

Measurement of the Input Variables $\dot{V}_G$ is determined from the difference in the volume/time of G inspired ($\dot{V}I_G$) and that expired ($\dot{V}E_G$) with each breath, as follows:

$$\dot{V}_G = \dot{V}I_G - \dot{V}E_G \qquad \text{Equation (24)}$$

This equation can be modified to include the rate of washin or washout of G from the alveolar gas compartment (Wessel et al 1979), which is given by:

$$\frac{dPE'_{G_t}}{dt} \cdot \frac{Veff_G}{PB} \qquad \text{Equation (25)}$$

where $PE'_G$ is the measured partial pressure of G in end-tidal gas, and $Veff_G$ is the effective lung volume for G, so that $$\dot{V}_G = \dot{V}I_G - \dot{V}E_G - \frac{dPE'_{G_t}}{dt} \cdot \frac{Veff_G}{PB} \qquad \text{Equation (26)}$$

The rate of change of $$PE'_G \left(\frac{dPE'_G}{dt}\right)$$

can be estimated from the measured change of $PE'_G$ over a series of 3 breaths whose duration is measured by a timer. The pattern of change over the 3 breaths can be analysed using an appropriate least squares analysis technique, and assuming that the change follows an exponential washin/washout pattern, to obtain the approximate slope of the tangent to the exponential curve, which is $$\frac{dPE'_G}{dt}.$$

The determination of $\dot{Q}c$ is necessarily delayed by 2 breaths if this is done. Simpler alternatives that avoid this delay can be used with little loss of accuracy, such as taking a simple linear measurement of the change in $PE'_G$ between the current breath and the previous breath, with or without an appropriate modifier. Other alternatives include employment of system identification methods such as those described in standard texts (Ljung 1999).

If $CO_2$ is selected as the gas species G, then equation (26) can be simplified because $CO_2$ is not present in the inspired gas mixture under normal operating conditions (i.e., $\dot{V}_{I_G}$ is zero). This substantially improves the accuracy and precision of gas flow measurement and therefore of the final determination of cardiac output. Therefore, for $CO_2$:

$$\dot{V}A_{CO_2} = -\dot{V}E_{CO_2} - \frac{dPE'_{CO_{2t}}}{dt} \cdot \frac{Veff_{CO_2}}{PB} \qquad \text{Equation (27)}$$

Both $\dot{V}_{I_G}$ and $\dot{V}_{E_G}$ can be measured in a number of ways. The ideal approach allows immediate measurement with each breath.

Total gas flow rate is measured using a pneumotachograph, or other device for the measurement of gas flow within a hollow tube (such as a differential pressure transducer, hot wire anemometer, turbine anemometer or other device). Gas concentration is measured by sidestream sampling or inline measurement by a rapid gas analyser. Suitable gas analysers include infrared absorption devices, photoacoustic devices, mass spectrometers, paramagnetic devices, Raman scatter analysers or other devices.

The volume of the gas G inspired and expired with each breath is obtained by multiplying flow by concentration point by point in time, and integrating the resultant waveform with respect to time. Accuracy is improved by compensating for transport delay (with sidestream sampling) and response time of the gas analyser. For example, if inspiration takes place between times $t_1$ and $t_2$, and expiration between $t_2$ and $t_3$ $$\dot{V}I_G = \frac{\int_{t_1}^{t_2} \dot{V}I_t \cdot P_{G_t} \cdot dt}{PB \cdot (t_2 - t_1)} \qquad \text{Equation (28)}$$

and $$\dot{V}E_G = \frac{\int_{t_2}^{t_3} \dot{V}E_t \cdot P_{G_t} \cdot dt}{PB \cdot (t_3 - t_2)} \qquad \text{Equation (29)}$$

where $\dot{V}_{I_t}$ and $\dot{V}_{E_t}$ are the measured total gas flow rates at time t during inspiration and expiration respectively. $P_{G_t}$ is the measured partial pressure of G at the point of gas sampling at time t.

Total gas flow measurement can be determined by measuring the concentration of a marker gas M fed into the gas stream at a known flow rate. This is usually an insoluble gas such as nitrogen, argon or sulphur hexafluoride, which is not taken up by the lungs. For example, the expiratory total gas flow rate at time t can be measured from:

$$\dot{V}E_t = \frac{\dot{V}EM_t}{PEM_t} \cdot PB \qquad \text{Equation (30)}$$

where $\dot{V}E_{M_t}$ is the known flow rate of the marker gas M, and $P_{EM_t}$ is its measured partial pressure at time t. The inspiratory total gas flow rate can be determined from a similar equation.

Improved accuracy of measurement of total gas flow rates, and therefore of $\dot{V}_G$, can be obtained if flow and gas concentration are measured at other locations in the breathing system, where tidal variations in gas concentration have been removed by thorough mixing of expired gas prior to sampling (such as by the presence of a length of mixing tubing, mixing box, mechanical baffles or an agitator, such as a fan, in the breathing circuit). Thus $\dot{V}E_t$ can be determined by:

$$\dot{V}E_t = \frac{\dot{V}EM_t}{\overline{PEM}_t} \cdot PB \qquad \text{Equation (31)}$$

where $\overline{PEM}_t$ is the mean partial pressure of M in mixed expired gas. This provides a mean expired flow measurement which may be more stable and accurate than the tracking tidal flows determined by equations of the form of equation (28) or (29), because rapid signal sampling and more complex data processing can be dispensed with. On the other hand, this can be expected to dampen the response of the gas exchange measurement to the breath by breath changes in gas exchange preferred for the capnotracking method. A potentially useful approximation for the volume of expired $CO_2$ with each breath can be obtained from the delivered tidal volume, adjusted for deadspace, and multiplied by the measured fractional concentration of alveolar $CO_2$.

Other methods of measurement of gas exchange that are less ideal but possible to employ include volume displacement methods in which the change in volume of a calibrated device such as concertina bag or spirometer is measured over a known time span to obtain net gas uptake from a circuit. It will be apparent to those skilled in the art that these and other methods can be used for the measurement of gas exchange by the lungs.

$P_{E'_G}$ can be measured at the end of each expired breath from a standard expirograph tracing for G. The value of $P_{E'_G}$ is taken from a defined point on the plateau of the expirograph waveform, reflecting the end-expired (end-tidal) partial pressure of G. For $CO_2$, this lies at or near the top of the curve for each breath.

Correction for Changes in Alveolar Ventilation:

Another factor that will produce change in $\dot{V}_G$, in the absence of a real change in $\dot{Q}t$ is a change in the level of ventilation of the lungs ($\dot{V}$). Because of the large $CO_2$ stores in the body, this change in $\dot{V}_{CO_2}$ can be relatively prolonged, but will gradually disappear as $\dot{V}_{CO_2}$ approaches its original value prior to the change in $\dot{V}$. This steady state value of $\dot{V}_{CO_2}$ is largely dictated by metabolic $CO_2$ production, and will approximate the value of $\dot{V}_{CO_2}$ at the point of the previous calibration, $\dot{V}_{CO_{2i}}$. The measured $\dot{V}_{CO_2}$ at time t($\dot{V}_{CO_{2t}}$) following the change in $\dot{V}$ from $\dot{V}_i$ to $\dot{V}_k$, will approach $\dot{V}_{CO_{2i}}$ in an approximately exponential manner, according to:

$$\frac{d\dot{V}_{CO_2}}{dt} = -K(\dot{V}_{CO_{2t}} - \dot{V}_{CO_{2i}}) \qquad \text{Equation (32)}$$

where K is the reciprocal of the time constant of washout or retention of $CO_2$ by body tissue stores. The value of K can be estimated from the expected time constant, which is the ratio of $\nabla_{CO_2}$ to body tissue $CO_2$ stores ($V_{CO_2body}$):

$$K = \frac{\dot{V}_{CO_2}}{V_{CO_2body}} \qquad \text{Equation (33)}$$

The $V_{CO_2body}$ of relevance refers to $CO_2$ stores in the well-perfused or "vessel-rich" regions of the body, namely the vital organs in the anaesthetised or immobile patient. These will have a much shorter time constant than the remainder of the body tissues.

Alternatively, K can be estimated from the initial rate of change of $\dot{V}_{CO_2}$ following the change in $\dot{V}$ and linear extrapolation, as follows:

$$K = \frac{\frac{d\dot{V}_{CO_2}}{dt}\text{initial}}{\dot{V}_{CO_{2i}} \cdot \left(\frac{\dot{V}_k}{\dot{V}_i} - 1\right)} \qquad \text{Equation (34)}$$

Experimentally, values of K of around 0.05/min are typical of an adult patient. From integration of equation (31) with respect to t, correction to $\dot{V}_{CO_2}$ can be made in real time from the estimate it provides of the change in $\dot{V}_{CO_2}$ expected from the change in $\dot{V}$ alone between breaths i and k. If $\dot{V}_{CO_{2k}}$ is substituted for $\dot{V}_{CO_{2t}}$ $$\dot{V}_{CO_{2k}} \text{ corrected} = \dot{V}_{CO_{2k}} - \dot{V}_{CO_{2i}} \cdot \left(\frac{\dot{V}_k}{\dot{V}_i} - 1\right) e^{-Kt} \qquad \text{Equation (35)}$$

Subsequent recalibration is advisable within several minutes following a sustained change in $\dot{V}$.

Determination of $Veff_G$ $Veff_G$ is determined by the alveolar gas volume ($V_A$), along with the volume of lung tissue ($V_L$) and the solubility of the gas in lung tissue ($SL_G$). It will therefore be different for gases of different solubilities. Methods for the determination of $Veff_G$ are described below.

(i) Determination of $Veff_G$ by Estimation from Published Data

The first method described below uses published data (McDonnell and Seal 1991, Brudin et al 1994). However a number of different methods are known and accepted for use to estimate lung volume and can be used with the capnotracking method described herein. The first method is derived from the simplified model of the lung referred to above, i.e., a single compartment consisting of alveolar gas and lung tissue and pulmonary capillary blood in equilibrium with one another. The volume of the alveolar gas is $V_A$ and the volume of lung tissue is $V_L$. With each tidal breath, gas enters the compartment during inspiration, and leaves during expiration. The volume of each breath is the "tidal volume" ($V_T$). Mixed venous blood from the body tissues arrives at the compartment, and after achieving equilibrium with the alveolar gas mixture in the pulmonary capillaries, leaves as pulmonary end-capillary blood. This flow of blood, which engages in gas exchange with the inspired alveolar gas, is the "non-shunt" or "effective pulmonary capillary blood flow" $\dot{Q}c$. In addition, mixed venous blood that bypasses the alveolar gas compartment ("shunt" $\dot{Q}s$) will mix with this pulmonary end-capillary blood to form arterial blood, which travels to the body tissues as the cardiac output ($\dot{Q}t$). A gas species G enters the compartment in inspired gas and mixed venous blood, and is removed from it in pulmonary end-capillary blood or expired alveolar gas.

$Veff_G$, the effective volume of distribution of a gas in the lung, is determined by $V_A$, $V_L$ and the solubility of the gas in lung tissue ($SL_G$). These parameters can be estimated from body height, weight, sex and other patient demographic data and the known solubility of the gas in lung tissue.

However, for a gas eliminated by the lung, $Veff_G$ is modified by the presence of shunt, which can be significant in anaesthetised or critically ill patients. Those areas of lung that contain shunted blood do not contribute to gas exchange, and therefore do not contribute to the effective volume of distribution of gas, such as $CO_2$, which diffuses from blood into the alveolar gas compartment.

$Veff_G$ can be estimated for adults as follows. $V_L$, the volume of lung tissue, is typically 0.5 liters, and for simplicity can be assumed to be proportional to body surface area (BSA). However, once again, those areas of lung tissue contained in shunting regions of the lung will not contribute to effective lung volume. So that:

$$VL = 0.5 \cdot \frac{BSA}{1.8} \cdot \left(1 - \frac{\dot{Q}s}{\dot{Q}t}\right) \qquad \text{Equation (A1)}$$

with $$BSA = \sqrt{\frac{Wt \cdot Ht}{36}} \qquad \text{Equation (A2)}$$

where Wt is the body weight in kg, Ht is the height in meters, and the shunt fraction ($\dot{Q}s/\dot{Q}t$) can be determined as set out further below.

From the data of McDonnell and Seal (McDonnell and Seal 1991) for adults:

$$VA = 0.825 \cdot \frac{M}{3.34} \cdot \left[5.18 \cdot Ht + 0.11 \cdot \left(\frac{Wt}{Ht^2} - 23\right) - 6.24\right] \qquad \text{Equation (A3)}$$

where M is a modifier for the patient's sex: M is 3.34 for males and 2.86 for females. The scaling factor 0.825 represents the decrease in lung volume that occurs in all patients when anaesthetised (Nunn 1993).

Equation (A3) provides a value for the patient's resting lung volume, but can be augmented further by an adjustment for the tidal volume ($V_T$). $V_A$ is the time weighted mean of the value obtained from equation (A3) and that value can be augmented by $V_T$, as follows:

$$V_A = V_A + V_T \cdot (I:E) \qquad \text{Equation (A4)}$$

where I:E is the inspiratory to expiratory ratio of each breath, typically 1:2 or 0.33.

$V_A$ is further modified by an adjustment ($\Delta V_A$) representing the proportion of alveolar gas volume contained in shunting areas of the lung. This will generally be a small proportion, but can be estimated from the data of Brudin (Brudin et al 1994) which relates the distribution of gas volume to blood volume in the lung. For the sake of simplicity, the distribution of $V_L$ is assumed to parallel that of blood volume. Overall, $V_L$ is roughly 5/6 of the blood volume, so that from Brudin:

$$VL \cdot \frac{\dot{Q}s}{\dot{Q}t} = \frac{5}{6} \cdot [0.16 + \log_e \Delta VA - 0.05 \cdot \Delta VA] \qquad \text{Equation (A5)}$$

This equation is evaluated iteratively to solve for $\Delta V_A$ given the value for $V_L$ and shunt fraction, which can be determined as described further below. Finally:

$$Veff_G = V_A - \Delta V_A + V_L \cdot SL_G \qquad \text{Equation (A6)}$$

For $CO_2$:

$$Veff_{CO_2} = V_A - \Delta V_A + V_L \cdot S_{L_{CO_2}} \qquad \text{Equation (A7)}$$

The concentration of gas in the alveolar deadspace is always the same as in the inspired gas mixture, and does not alter in response the changes in alveolar ventilation or gas exchange. However, because $P_{E'_G}$ already reflects the volume weighted partial pressures of G from both alveolar and alveolar deadspace compartments, $Veff_G$ is not further reduced in proportion to the alveolar deadspace volume.

(ii) Determination of $Veff_G$ by Inert Gas Dilution.

A standard method of measurement of $Veff_G$ is by insoluble inert gas dilution ("washin"). This is used in established methods for measurement of $\dot{Q}c$ by inert soluble gas uptake, such as acetylene or nitrous oxide rebreathing techniques (Cander and Forster 1959, Petrini et al 1978, Hook et al 1982, Gabrielsen et al 2002). An insoluble gas, which is not absorbed significantly by the blood, is administered simultaneously with the soluble gas. The measured change in concentration of the insoluble gas reflects the dilution of the inspired gas mixture throughout the effective lung volume, enabling the determination of $V_A$. Estimation of $V_L$ is also required and this is done by other methods, such as extrapolation of soluble gas concentration change to time zero for the manoeuvre, to indicate uptake by lung tissues, which is assumed to be rapid compared with uptake by the blood.

Such techniques can be applied to estimation of $Veff_G$, either as an initial "once off" or as an intermittent manoeuvre, as part of a continuous cardiac output monitoring system, such as the system described herein.

A System for Monitoring Cardiac Output

The capnotracking method can be implemented using standard hardware components available on essentially any modem anaesthesia workstation, and can be readily incorporated into any existing integrated modem platform, using software modifications only.

Figure 2:
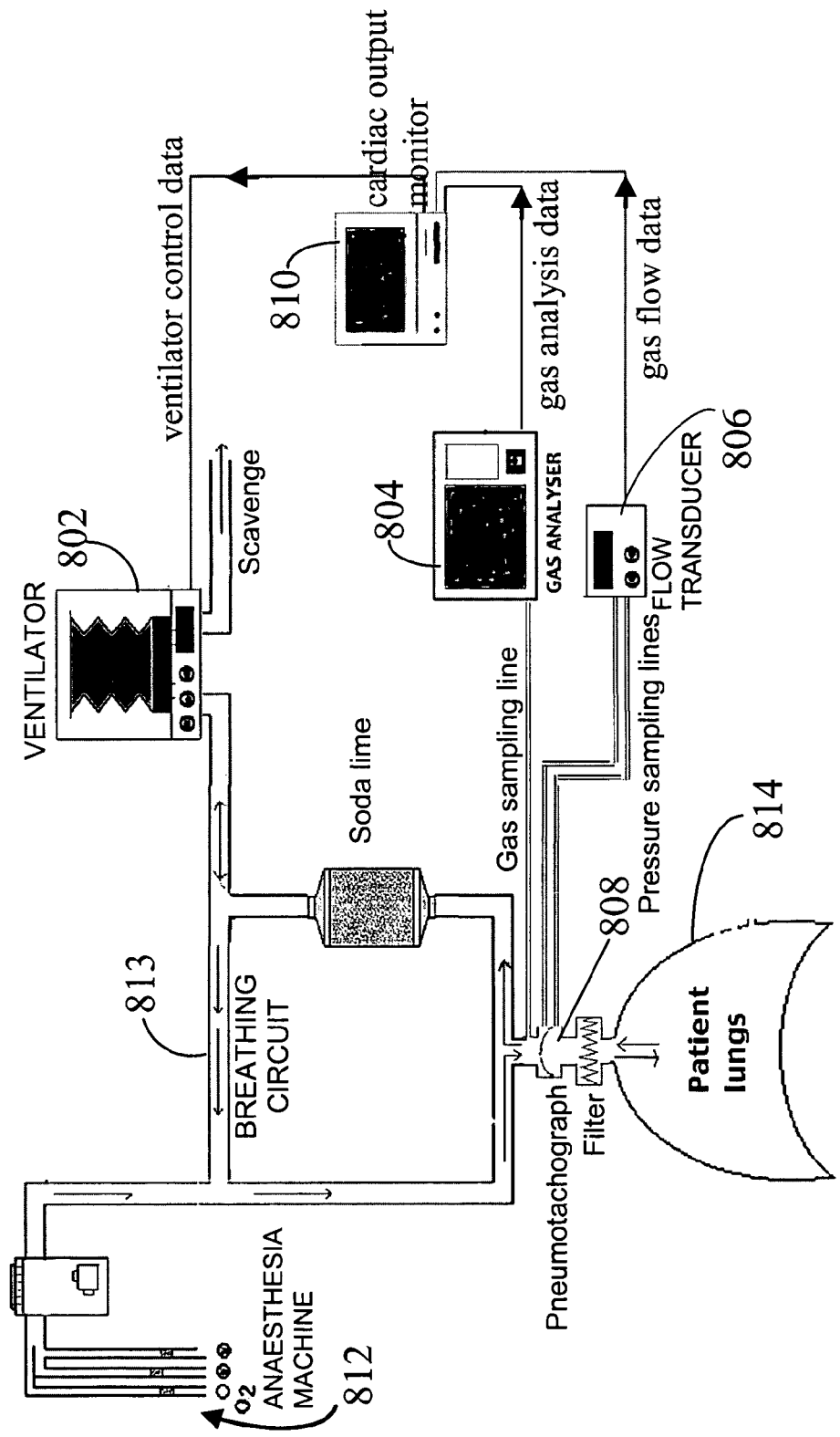
FIG. 2 is a schematic diagram of a system for monitoring cardiac output in accordance with one embodiment of the present invention, wherein the system controls a ventilator to produce changes in alveolar ventilation.

As shown in FIG. 2, a system for monitoring cardiac output includes a rapid gas analyser 804 (Datex Capnomac Ultima, Datex-Ohmeda, Finland), a gas flow transducer 806 (Validyne Corp, USA), and a gas flow measurement device 808 (such as a Fleisch pneumotachograph (Hans Rudolf Corp, USA)), including side stream gas concentration sampling port for the gas analyser 804, and a cardiac output monitor 810. As shown in FIG. 2, the system is also interconnected with a typical anaesthesia delivery system, including an anaesthesia machine 812, a ventilator 802 (Ohmeda 7800 ventilator, modified to be controlled by the cardiac output monitor 810), and breathing circuit 813, connected to a common mouthpiece or other gas pathway of the breathing circuit, which is attached to a patient in order to provide gas to lungs 814 of the patient, and to receive exhaled gas from those lungs 814.

Figure 3:
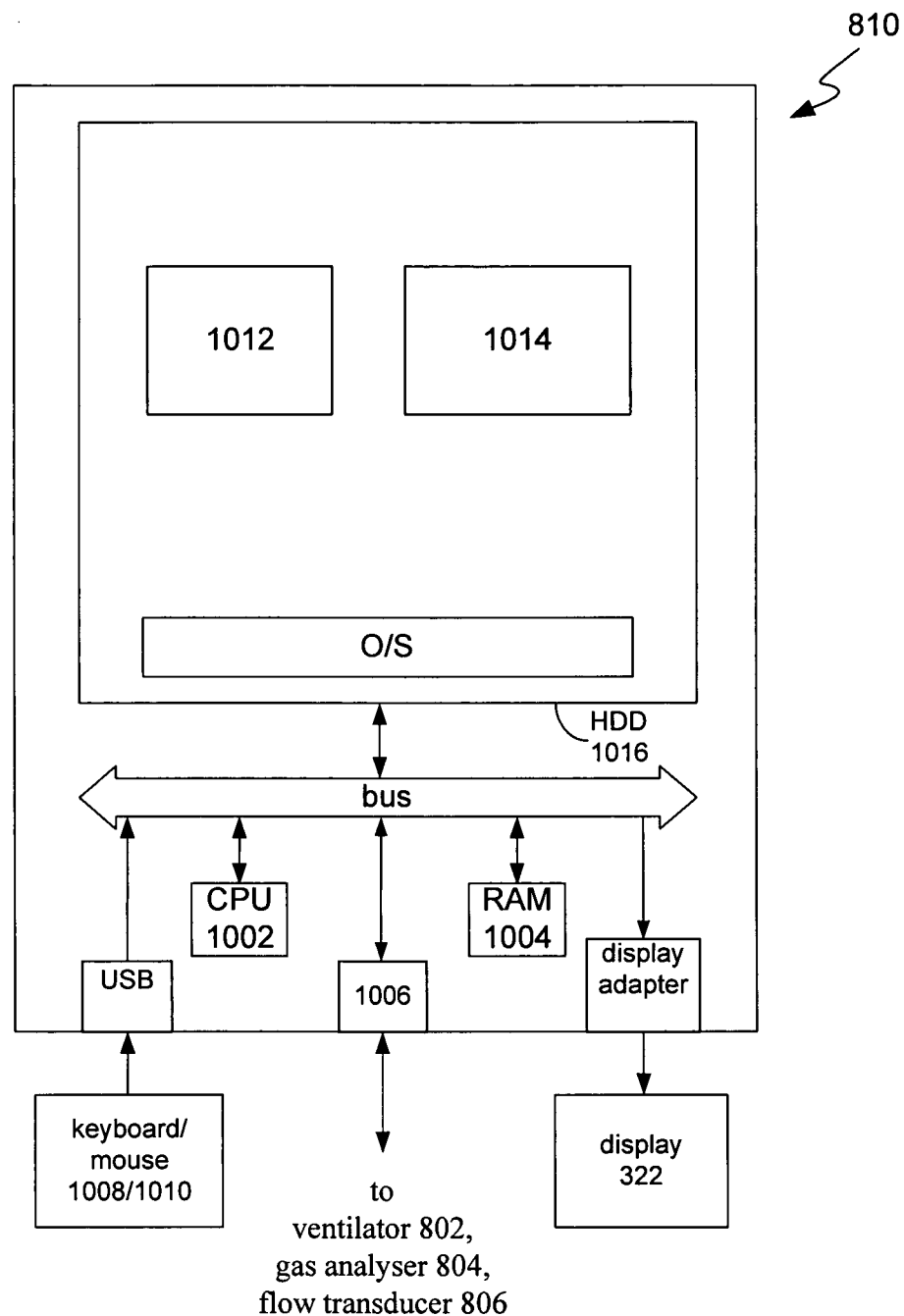
FIG. 3 is a block diagram of a cardiac output monitor of the system.

In its preferred embodiment, the cardiac output monitor 810 executes a method for monitoring cardiac output ($\dot{Q}t$) that first determines a baseline or "calibration" $\dot{Q}t$ ($\dot{Q}t_i$), following which a continuous, breath-by-breath measurement of $\dot{Q}t$ is obtainable. In the described embodiment, the cardiac output monitor 810 is a standard computer system, and the cardiac output monitoring method is implemented in software developed using the LabVIEW graphical programming environment for data acquisition and instrument control, available from National Instruments Corporation, USA. As shown in FIG. 3, the computer 810 includes at least one processor 1002, random access memory 1004, at least one input/output interface 1006 for interfacing with the ventilator 802, the gas analyser 804, and the flow transducer 806, a keyboard 1008, a pointing device such as a mouse 1010, and a display 1011.

The cardiac output monitor 810 also includes the LabVIEW software development application 1012, and the cardiac output monitoring method is implemented as one or more LabVIEW software modules, being the cardiac output modules 1014 stored on non-volatile (e.g., hard disk) storage 1016 associated with the computer system 810. However, it will be apparent to those skilled in the art that the various components of the cardiac output monitoring system can be distributed over a variety of locations and in various combinations, and that at least part of the cardiac output monitoring method could alternatively be implemented by one or more dedicated hardware components such as application-specific integrated circuits (ASICs) or field-programmable gate arrays (FPGAs).

Figure 4:
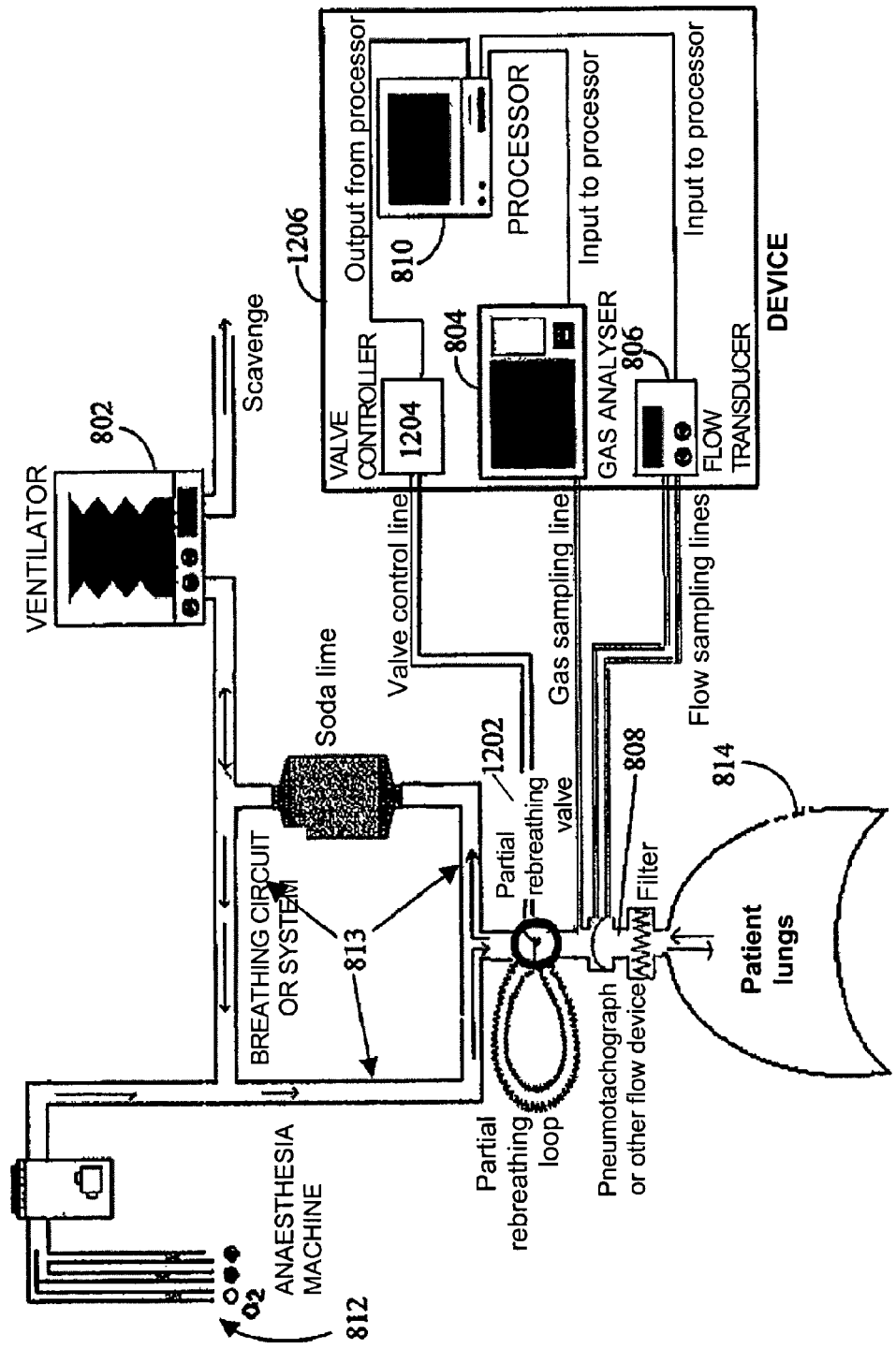
FIG. 4 is a schematic diagram of a system for monitoring cardiac output in accordance with an alternative embodiment of the present invention, wherein the system controls a partial rebreathing valve to produce changes in alveolar ventilation.

As shown in FIG. 4, in an alternative embodiment, a system for monitoring cardiac output includes a length or loop of deadspace tubing opened to or closed from the breathing circuit by a partial rebreathing valve 1202 whose operation is controlled by the cardiac output monitor 810, via a valve controller 1204. Additionally, the gas analyser 804, gas flow transducer 806, and cardiac output monitor 810 are provided in a single housing or chassis 1206 to provide an integral, stand-alone cardiac output monitoring system that can be attached to any standard anaesthesia delivery system. Although the components 804, 806, and 810 are notionally the same as those in the previous embodiment shown in FIG. 1, it will be apparent that when those components are combined within a single chassis 1208, it may alternatively be preferable to select alternative versions of these components to make the integrated stand-alone system more compact and to improve its ergonomics.

In the embodiment shown in FIG. 4, the pneumotachograph/gas sampling line 808 is positioned between the patient's lungs 814 and the partial rebreathing valve 1202, and consequently Equation (24) or (26) is used in this embodiment to determine the uptake or elimination of $CO_2$ because the patient will rebreathe a substantial amount of exhaled $CO_2$ with each inspired breath. However, if the partial rebreathing valve 1202 is alternatively located between the patient's lungs 814 and the pneumotachograph/gas sampling line 808, the simpler Equation (27) can be used because the amount of rebreathed $CO_2$ will be substantially reduced in this arrangement.

As shown in FIG. 2, the cardiac monitor 810 receives gas analysis data from the rapid gas analyser 804, and gas flow data from the flow transducer 806. The cardiac monitor 810 also generates and outputs ventilator control data to control the ventilator 802 and thereby the alveolar ventilation of the patient's lungs 814. However, it will be apparent that alternatively the ventilator could be independently configured to adjust the alveolar ventilation in a predetermined manner, and to provide an output signal to the cardiac monitor 810 to indicate these changes.

Determination of Baseline "Calibration" Cardiac Output.

Figure 5:
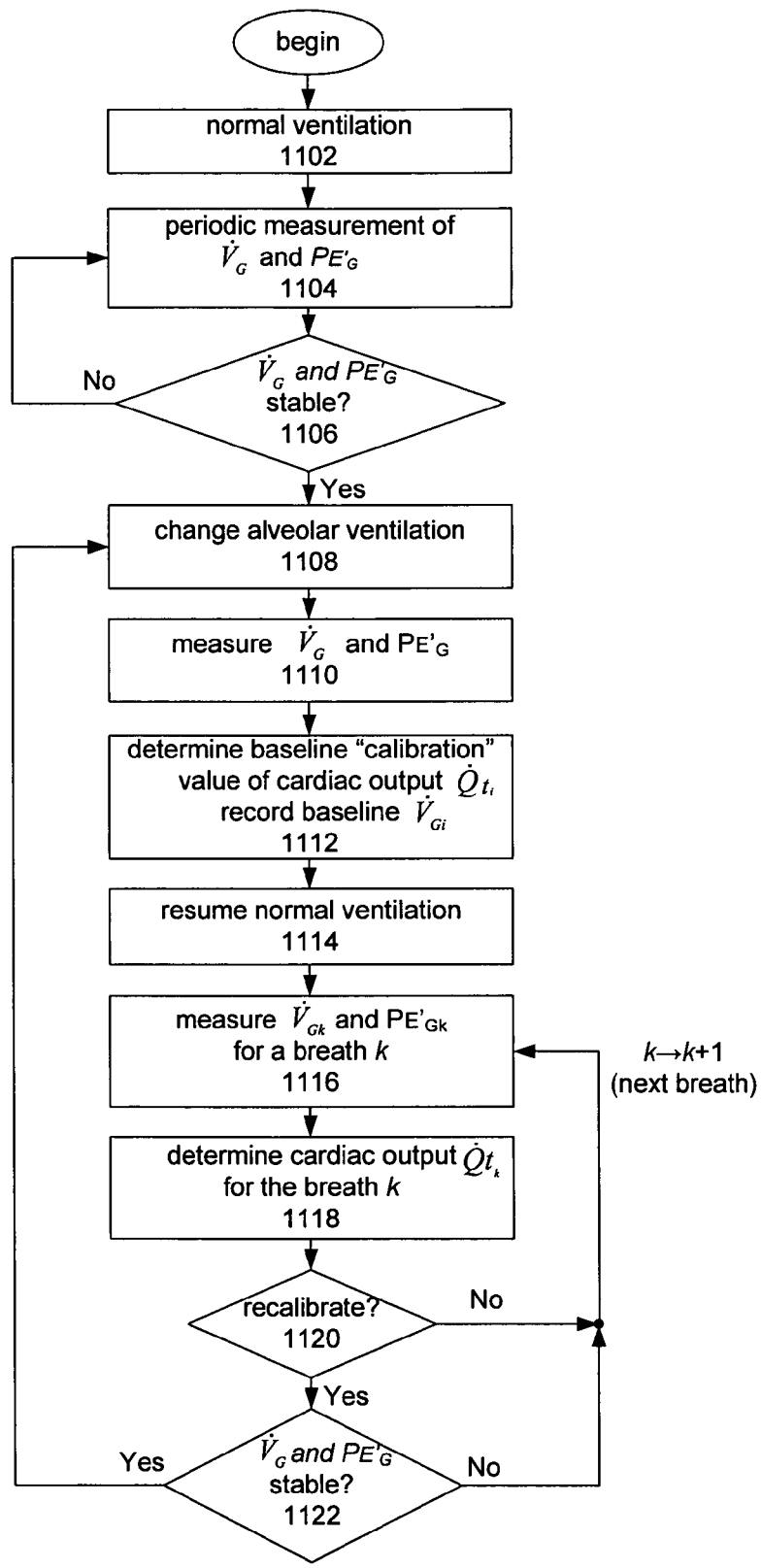
FIG. 5 is a flow diagram of a method for monitoring cardiac output executed by the system in accordance with one embodiment of the present invention.

As shown in FIG. 5, in a preferred embodiment the cardiac output monitoring method begins at steps 1102 and 1104 by beginning the periodic measurement of the end-tidal partial pressure $P_{E'_G}$ and the rate of uptake or elimination $\dot{V}_G$ of the gas species G of interest. Total flow rates within the breathing system are measured by the flow transducer 806, which generates gas flow data representing these flow rates and sends that data to the cardiac monitor 810. The gas breathed by the patient is analysed by the rapid gas analyser 804, which generates gas analysis data representing the results of that analysis, and sends that data to the cardiac monitor 810 for processing. The gas flow data and the gas analysis data are generated and sent in real-time on a breath by breath basis to the cardiac monitor 810, which processes the received data to determine $P_{E'_G}$, the end-tidal partial pressure, and $\dot{V}_G$, the rate of uptake or elimination of the gas species G.

At step 1106, the cardiac output monitor 810 assesses the stability of these physiological parameters according to pre-determined criteria. For example, a consecutive series of 6 or more measurements with a standard error of less than 2% relative can be taken to indicate a stable physiological parameter. If these parameters are assessed to be stable, then these values of $P_{E'_G}$ and $\dot{V}_G$ are stored (as $P_{E'_{G_i}}$ and $\dot{V}_{G_i}$), and a stepwise change in alveolar ventilation of the lungs is then made at 1108 for a brief period of time, as described below, and at step 1110 $\dot{V}_G$ and $P_{E'_G}$ are measured under this changed ventilation condition. At step 1112, $\dot{Q}c$ is determined using equation (5), and $\dot{Q}t$ is then determined from $\dot{Q}c$, using an estimate of shunt fraction, as described above, providing the baseline "calibration" value for $\dot{Q}t$ ($\dot{Q}t_i$). At step 1114, the level of alveolar ventilation is then returned to its baseline level, and at step 1116 the end-tidal partial pressure and the rate of uptake or elimination of G are measured again.

The acute changes in $\dot{V}_G$ and $P_{E'_G}$ that can be used to obtain the baseline "calibration" value for $\dot{Q}t$ ($\dot{Q}t_i$) are produced by inducing sudden changes in the level of alveolar ventilation of the lungs. This can be achieved in a number of ways. In patients who are undergoing controlled ventilation by an automated ventilator, such as patients under anaesthesia or in intensive care, this can be done, for example, by altering respiratory rate and I:E (inspiratory to expiratory) ratio or the duration of end-expiratory pause according to the method of Gedeon (Gedeon et al 1978). Alternatively, a stepwise change can be made in the tidal volume. These methods generally require automated control of an electronic ventilator, as shown in the embodiment of FIG. 2.

However, the alternative embodiment of the cardiac output monitoring system shown in FIG. 4 produces changes in the level of the alveolar ventilation by intermittently introducing a volume of serial deadspace into the breathing system, specifically by opening and closing a partial rebreathing valve 1202 attached to a length or loop of deadspace tubing. By altering the serial dead space in breathing system (VD), the level of alveolar ventilation is altered in the opposite direction. This method can be used in patients who are not undergoing controlled ventilation, but are breathing spontaneously. It is also possible, although less practical, to produce the acute change in $\dot{V}_G$ and $P_{E'_G}$ by means other than altering alveolar ventilation, e.g., by intermittently adding a gas species G ($CO_2$ or other gas) to the inspired gas mixture to alter its inspired concentration, in which case equations (18) or (19) are used for the continuous monitoring of cardiac output.

To improve the reliability (precision) of the measurement of $\dot{Q}c$, and therefore of $\dot{Q}t_i$, $P_{E'_G}$ and $\dot{V}_G$ can be averaged over the last 2 or more breaths of the period of change in ventilation. The period of ventilatory change from which the measurements of $P_{E'_G}$ and $\dot{V}_G$ are taken may be altered post hoc. For example, if the initial measurements suggest a high value for $\dot{Q}c$, the period of ventilatory change from which the measurements of $P_{E'_{CO_2}}$ and $\dot{V}_{CO_2}$ are taken can be shortened to reduce the effect of a rise in $\overline{Cv}_{CO_2}$ due to recirculation of $CO_2$, which will cause an erroneous underestimate of $\dot{Q}c$ if not corrected for (Yem et al).

The change in the alveolar ventilation is typically of the order of 50% or so (e.g., cyclic changes in tidal volume, or in the volume of serial deadspace in the breathing system, of 200 mL or so, or changes in respiratory rate of 5 breaths/min which may be accompanied by alterations in I:E ratio), although smaller or larger relative changes can be used. The larger the change, the greater the acute change in the variables measured to determine cardiac output ($\dot{V}_G$ and $P_{E'_G}$). Improved accuracy and precision of the determined cardiac output are expected from this, although practical limitations apply to the size of the tidal volumes or breath to breath intervals that can be used safely in a patient.

Although the baseline calibration value for $\dot{Q}t$ ($\dot{Q}t_i$) is described herein as being determined by methods employing equations such as equation (5), it will be apparent that the value for $\dot{Q}t_i$ could alternatively be determined using alternative methods, provided that $\dot{V}_G$ and $P_{E'_G}$ are nevertheless recorded at the time of the measurement.

Continuous Monitoring of Cardiac Output.

Referring to FIG. 5, having determined a baseline "calibration" value for $\dot{Q}t$ ($\dot{Q}t_1$), at step 1112 and values for $P_{E'_{G_i}}$ and $\dot{V}_{G_i}$, at step 1116, a continuity equation (being one or more of equations (19), (20), and (21)) is then used to determine updated values for $\dot{Q}t$ at a subsequent breath k ($\dot{Q}t_k$) at step 1118, using $\dot{V}_{G_k}$. Steps 1116 and 1118 are then repeated a number of times for successive breaths to provide breath-by-breath determination of cardiac output. After an appropriate delay (typically 3 minutes or more) to allow washin or washout of G to near completion following the change in alveolar ventilation, the process can return to step 1108 (via steps 1120 and 1122) and an updated calibration value for $\dot{Q}t$ ($\dot{Q}t_i$) obtained at step 1112 if, at step 1122, the method determines that the end-tidal partial pressure of the gas species G of interest (typically $CO_2$), and the rate uptake or elimination of G appear to be stable, as described above. This may necessitate a brief interruption in the continuous breath-by-breath determination of cardiac output while a new baseline is determined at steps 1108 to 1114.

By executing the above steps, the system determines the cardiac output of the patient on an effectively continuous, breath-by-breath basis. This is continually updated and displayed on the system monitor 1011 to allow medical or nursing staff to non-invasively monitor the patient's cardiac output during surgery, critical care, and other related procedures.

Smoothing Functions:

To reduce the effects of random measurement imprecision on $\dot{Q}t_k$, a moving average of $\dot{Q}t_k$ can optionally be used. This has the effect of delaying the responsiveness of the system to real-time changes in cardiac output, but provides substantially more stable results. Technical improvements in the measurement of input parameters which reduce random measurement imprecision may allow shorter averaging or none at all, thereby improving the real-time responsiveness of the system.

Example I

Continuous breath-by-breath determinations of cardiac output were made by the capnotracking method using the cardiac output monitoring system described herein. These values were compared on a breath by breath basis with simultaneous measurements by an indwelling ultrasonic flow probe placed on the ascending aorta or pulmonary artery in six ventilated sheep, ranging in weight from 35-45 kg, anaesthetised with isoflurane in oxygen-air. Cardiac output was manipulated using a dobutamine infusion alternating with esmolol boluses.

Figure 6:
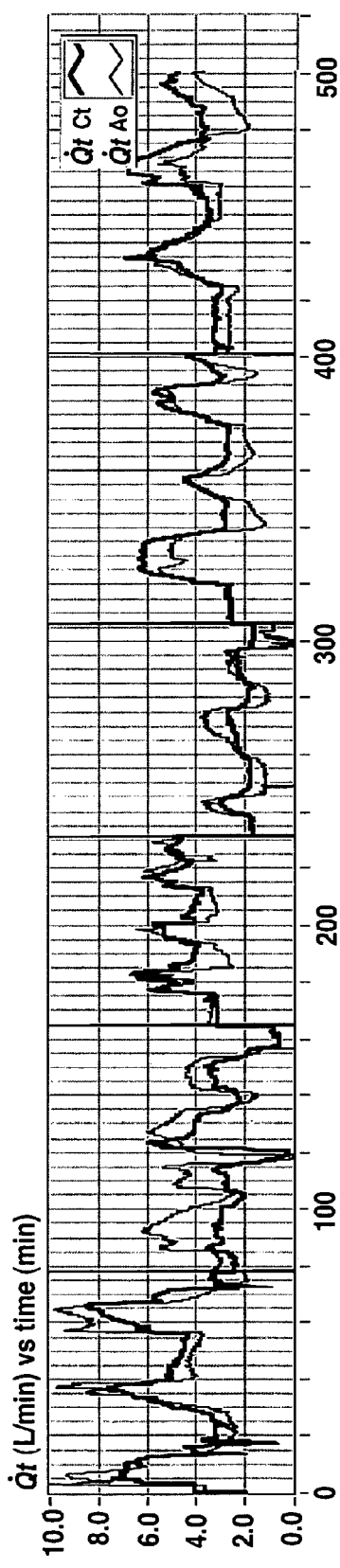
FIG. 6 is a graph of cardiac output as a function of time as measured by an indwelling ultrasonic flow probe, and as estimated by the capnotracking method of FIG. 5, being a composite graph of data from six anaesthetised sheep, in which the cardiac output was pharmacologically manipulated over a wide range.

$\dot{V}_{CO_2}$ and $P_{E'_{CO_2}}$ were measured with each breath, as described above. A single initial calibration cardiac output was measured by introducing a step change in tidal volume for 30 seconds and applying equation (5). Cardiac output was then determined breath-by-breath for up to 100 minutes, using the continuity equation (Equation (21)). FIG. 6 is a graph displaying cardiac output (l/min) as a function of time (mins) as determined by the capnotracking method (thick solid line), and as measured directly by an aortic flow probe (thin solid lines).

To assess the accuracy of the capnotracking method, the mean difference and the standard deviation [sd] of the difference in measurement of $\dot{Q}t$ between capnotracking ($\dot{Q}t_{Ct}$) and aortic flow probe ($\dot{Q}t_{Ao}$) measurements were determined, and intraclass correlation coefficients (ICC) were determined for (i) $\dot{Q}t$ with each breath; and (ii) changes in $\dot{Q}t$ between successive 5 minute periods.

As shown in FIG. 6, the cardiac output $\dot{Q}t$ measured by the indwelling flow probe ($\dot{Q}t_{Ao}$) varied between zero and 10.4 L/min (mean 3.6 L/min). Overall mean bias for $\dot{Q}t$ (capnotracking-aortic flow probe) was +0.15 L/min [95% confidence limits: ±0.04 L/min]. The standard deviation of the difference was 1.04 L/min, giving upper and lower limits of agreement of +2.2 and −1.9 L/min. ICC was 0.79. Two cardiac arrest events pharmacologically induced in one of the animals were clearly identifiable by the capnotracking method within 30-60 seconds of occurrence, as shown at 120 and 160 minutes in FIG. 6.

Figure 8:
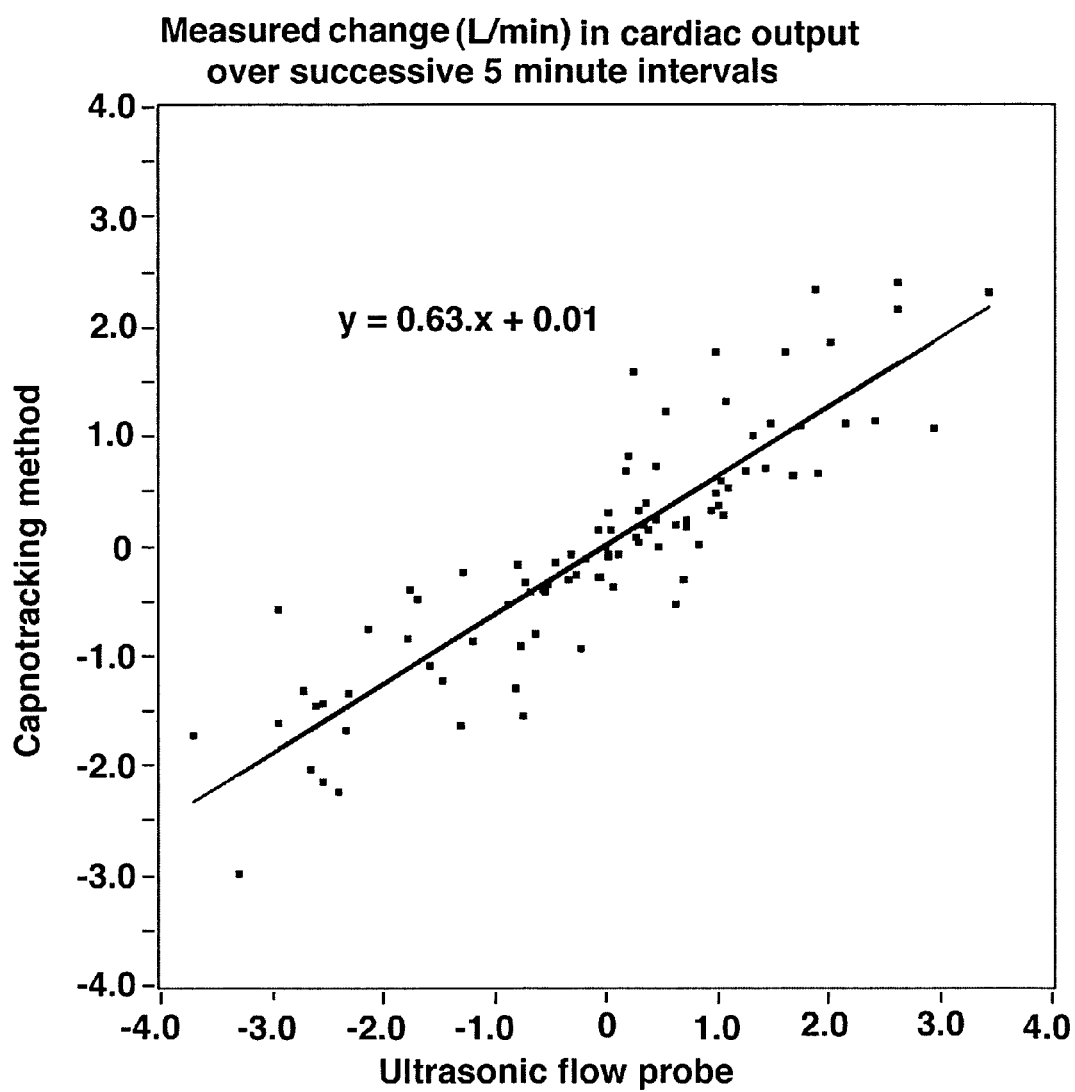
FIG. 8 is a graph showing the correlation between the ultrasonic flow probe measurements and the cardiac output values estimated by the capnotracking method described herein.

Mean bias for agreement in measured changes in $\dot{Q}t$ over successive 5 minute intervals was +0.03 L/min, with a standard deviation of the difference of 0.71 L/min. ICC was 0.84. FIG. 8 is a graph illustrating the correlation between measured and estimated changes in $\dot{Q}t$ over successive 5 minute intervals.

From the results of the above experiments, it was concluded that the cardiac output monitoring system had successfully tracked sudden dramatic fluctuations in cardiac output in real time in an animal model. The mean bias found is probably explained by coronary blood flow not measured by the aortic flow probe.

Comparison with the Prior Art Method of Orr et al.

Figure 7:
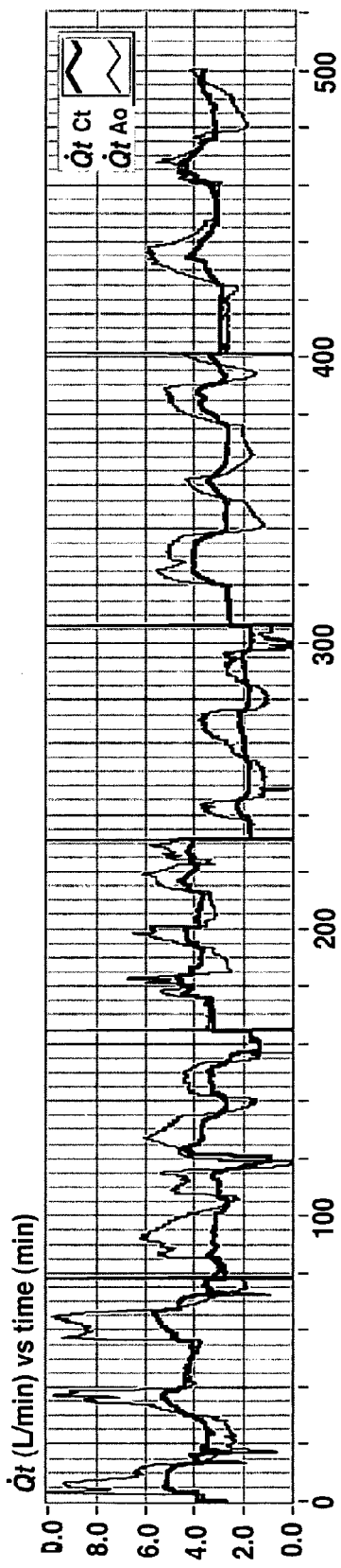
FIG. 7 a graph of cardiac output as a function of time as measured by an indwelling ultrasonic flow probe, and as estimated by the prior art method of Orr et al (U.S. Pat. No. 6,217,524 B1)
Figure 9:
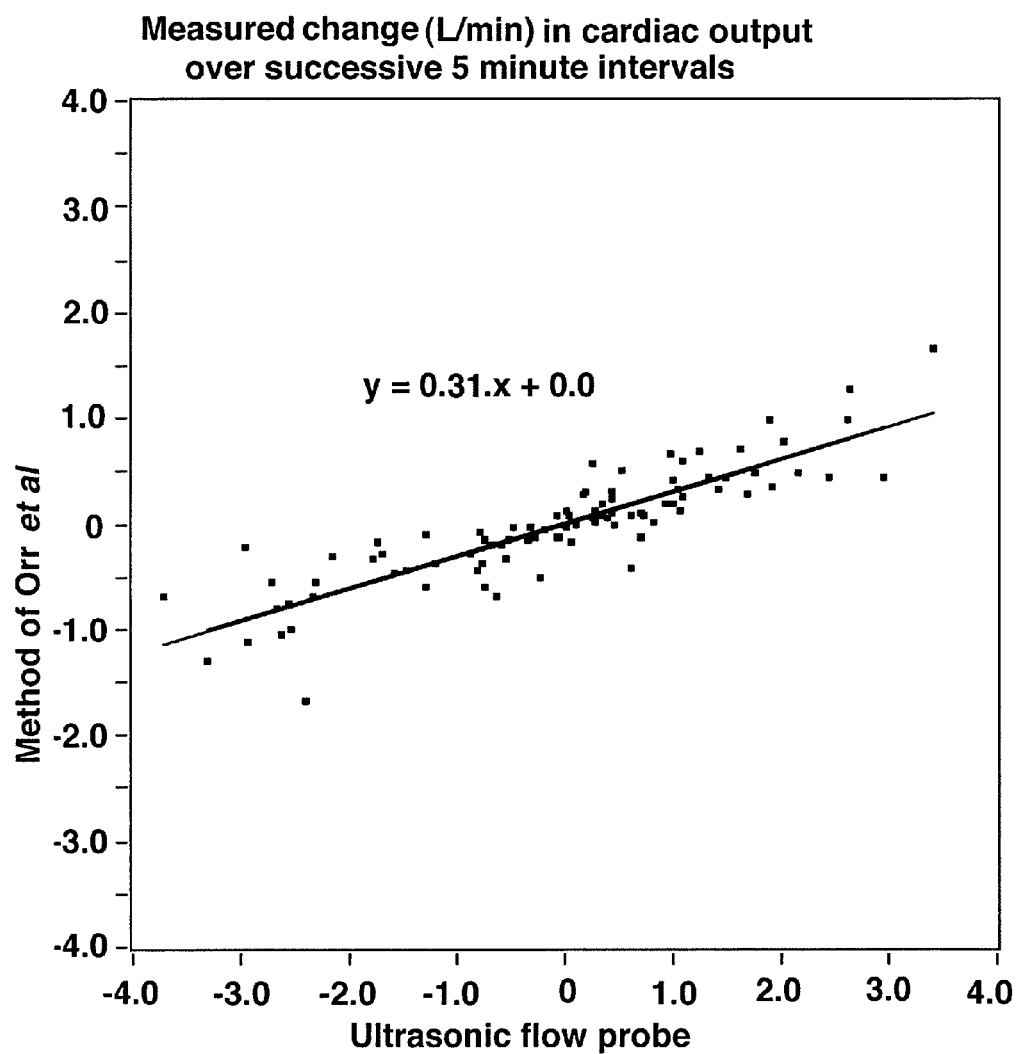
FIG. 9 is a graph showing the correlation between the ultrasonic flow probe measurements and the cardiac output values as estimated by the prior art method of Orr et al.

Comparison with the method described by Orr et al (U.S. Pat. No. 6,217,524 B 1) is useful to confirm the accuracy of the Capnotracking method and its improvement over existing techniques based upon measured $CO_2$ elimination by the lungs. The results of application of the equations described by Orr et al (Equations (7a & 7b)) to breath-by-breath tracking of $\dot{Q}t$ in this study are described above in the Background section of this specification and in FIGS. 7 and 9, and reveal a tendency to significantly underestimate the magnitude of real changes in cardiac output, due to the assumption that the arterio-venous $CO_2$ content difference is unchanged, and that a simple linear relationship follows between changes in $\dot{Q}t$ and changes in $\dot{V}_{CO_2}$. This may have serious consequences in the clinical situation. For example, in the scenario illustrated by the data points in FIG. 1, a potentially life-threatening fall in cardiac output from 8 L/min to 2 L/min, due to a medical emergency of some description, would be estimated by the method of Orr et al as a decline to 4 l/min. This may be considered by an attending physician to be within the normal range of cardiac output, prompting a delay in, or an inadequate response to, an actual emergency.

In contrast to their method, the capnotracking method described herein makes no assumptions about the stability of the arterio-venous $CO_2$ content difference. The derivation of Equation (21) allows for appropriate reciprocal changes in $\dot{V}_{CO_2}$ and arterio-venous $CO_2$ content difference dictated by the relationship between changes in $\dot{Q}t$ and these variables, as displayed in FIG. 1. The result is the far superior ability of Equation (21) to track important changes in $\dot{Q}t$ in real time.

Example II

Testing of the capnotracking method under clinical conditions has been conducted in patients undergoing cardiac surgery by way of comparison with bolus thermodilution (average of three 10 mL boluses of room temperature saline) in both pre- and post-cardiopulmonary bypass (CPB) periods. Data from 60 patients was collected, containing a total of 583 pairs of measurements (398 pre-CPB and 185 post-CPB).

Figure 10:
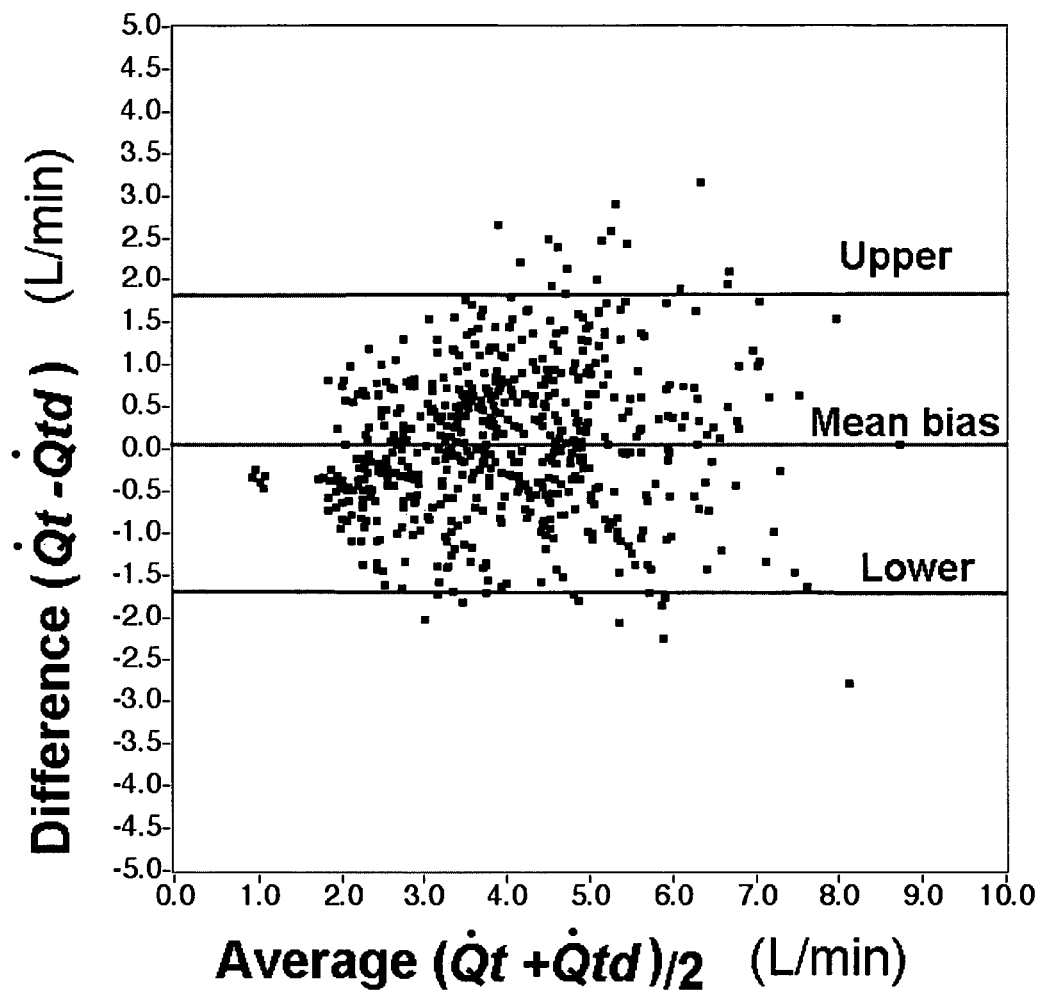
FIG. 10 is a Bland-Altman plot for simultaneous paired measurements of cardiac output made by the system ($\dot{Q}t$) and by bolus thermodilution ($\dot{Q}td$) in human patients undergoing cardiac surgery.
Figure 11:
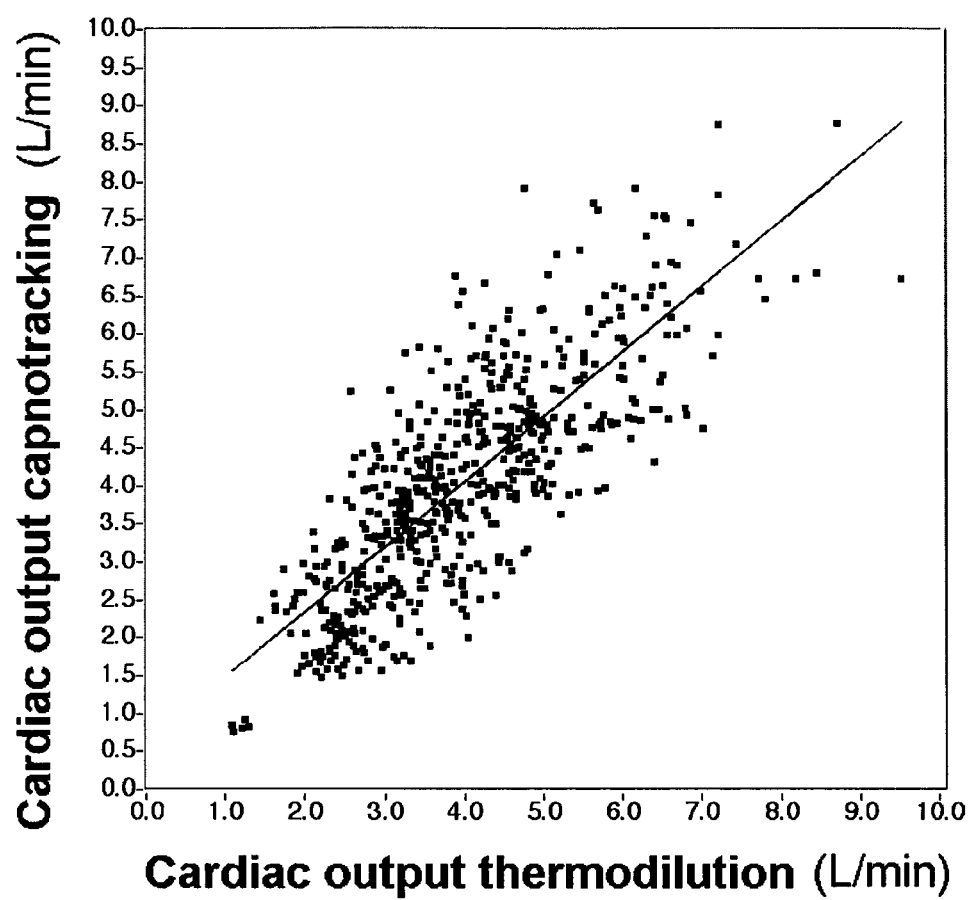
FIG. 11 is a correlation plot showing the relationship between the simultaneous paired measurements of FIG. 10, providing the relationship $\dot{Q}t=0.86 \cdot \dot{Q}td+0.64$ L/min.

Bland-Altman and correlation plots comparing the two methods are shown in FIGS. 10 and 11, respectively. The cardiac output as measured by bolus thermodilution ($\dot{Q}td$) ranged from 1.08 L/min to 9.51 L/min (mean 3.97 L/min). Mean bias ($\dot{Q}t-\dot{Q}td$) was +0.08 L/min. The standard deviation of the difference (sd) between paired measurements was 0.90 L/min, giving upper and lower limits of agreement with thermodilution of 1.84 L/min and −1.68 L/min respectively, r=0.79.

Regression analysis determined the relationship between the cardiac output values determined by the two methods to be $\dot{Q}t$=0.86. $\dot{Q}td$+0.64 L/min.

Data was stratified into "low $\dot{Q}td$" and "high $\dot{Q}td$" groups, which contained data where $\dot{Q}td$ was below and above the median value (3.80 L/min), respectively. In the low $\dot{Q}td$ group, the mean $\dot{Q}td$ was 2.91 L/min, and the mean difference (sd) was 0.20 (0.76) L/min. In the high $\dot{Q}td$ group, the mean $\dot{Q}td$ was 5.01 L/min, and the mean difference (sd) was −0.05 (1.00) L/min, suggesting that the scatter in agreement with thermodilution was related in a non-linear fashion to the absolute value of the cardiac output.

To examine the robustness of the system under different conditions, the data was further stratified into pre- and post-CPB measurements. Mean bias (sd) was +0.08 (0.84) L/min pre-CPB, and +0.07 (1.01) L/min post-CPB. Given the greater haemodynamic instability expected in the post-CPB period, and the greater difficulty in measurement, this data indicates that the method is capable of maintaining accuracy and precision in these circumstances.

Figure 12:
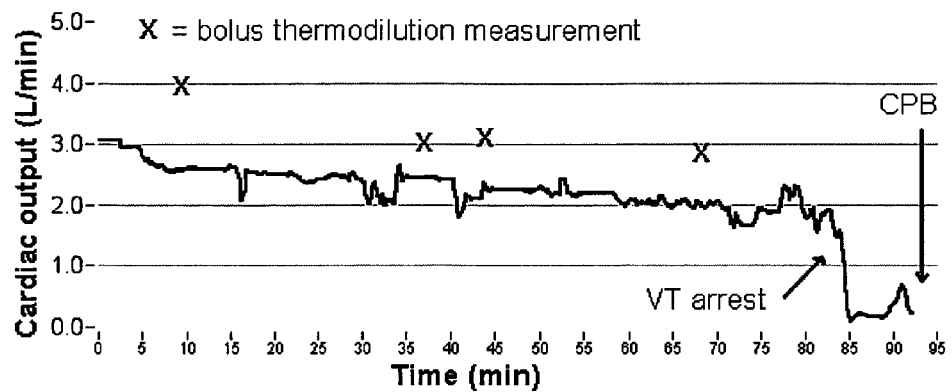
FIG. 12 is a graph of cardiac output as a function of time as determined by the system, demonstrating the real-time measurement capability of the system during an unexpected ventricular tachycardia (VT) cardiac arrest in a human patient prior to cardio-pulmonary bypass (CPB)

The ability of the capnotracking method to follow sudden unexpected changes in cardiac output in real time is demonstrated by the data in FIG. 12, collected in a patient undergoing coronary artery bypass graft surgery. After 80 minutes of graft harvesting with stable haemodynamics in sinus rhythm, the patient suddenly developed ventricular tachycardia (VT) with haemodynamic collapse. While urgent resuscitation and cannulation for CPB were performed, including repeated attempts at cardioversion, the patient was put onto CPB and surgery proceeded.

Figure 13:
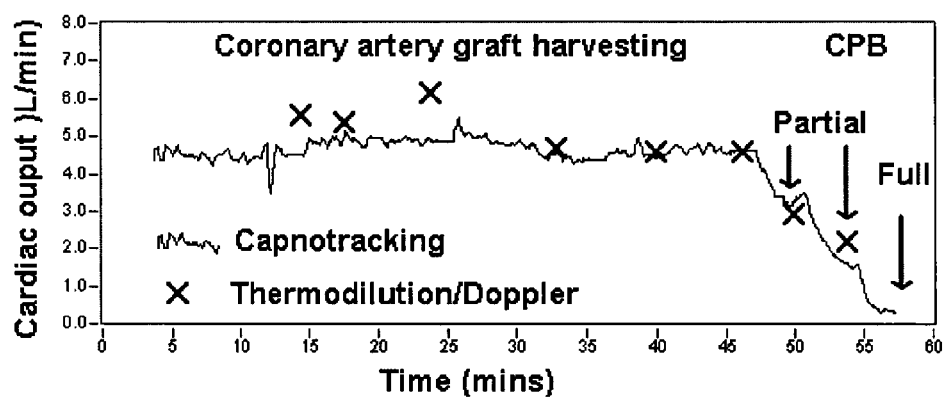
FIG. 13 is a graph of cardiac output as a function of time as determined by the system for a human patient in whom a staged run onto cardio-pulmonary bypass (CPB) was performed after completion of coronary artery graft harvest. Partial CPB at two increasing levels of venous drainage was instigated, and the cardiac output at each stage was also measured by transoesophageal echocardiography using pulse wave Doppler at the level of the left ventricular outflow tract (crosses). The acute falls produced in cardiac output were accurately captured prior to run onto full CPB. The system's slight underestimation of cardiac output at the lower level is expected due to the effect of acute haemodilution on the solubility of $CO_2$ in blood.

Similarly, the sudden fall in pulmonary blood flow accompanying run onto cardiopulmonary bypass was reliably captured by the capnotracking method. FIG. 13 shows data from a patient in whom a staged run onto CPB was performed after completion of coronary artery graft harvesting. Partial CPB at two increasing levels of venous drainage was undertaken, and the cardiac output at each stage measured by transoesophageal echocardiography using pulse wave Doppler at the level of the left ventricular outflow tract. The acute falls produced in cardiac output were accurately represented prior to run onto full CPB. This data confirms that the capnotracking method delivers the same kind of accurate real-time cardiac output monitoring observed in a sheep model, as described above.

Comparison with Other Techniques

The agreement with the indwelling flow probe in the sheep model, which provides an in vivo gold standard for comparison, confirms that the capnotracking method successfully delivers real time cardiac output monitoring. As is the case in all clinical studies of this nature, interpretation of the results in patients is limited by the imperfect accuracy and precision of thermodilution as the reference standard. Nonetheless, the accuracy and precision of agreement with thermodilution is as good as that achieved by other available methods, such as the newer generation pulse contour and Doppler devices, which are more invasive, expensive and labour intensive to apply.

Many modifications will be apparent to those skilled in the art without departing from the scope of the present invention as herein described with reference to the accompanying drawings.

REFERENCES

Brudin L H, Rhodes C G, Valind S O, Jones T, Jonson B and Hughes J M B. Relationships between regional ventilation and vascular and extravascular volume in supine humans. *J Appl Physiol.* 76(3): 1195-1204, 1994

Brudin L H, Rhodes C G, Valind S O, Jones T, and Hughes J M B. Interrelationships between regional blood flow, blood volume and ventilation in supine humans. *J Appl Physiol.* 76(3): 1195-1204, 1994

Cander L, Forster R E. Determination of pulmonary parenchymal tissue volume and pulmonary capillary blood flow in man. *J Appl Physiol.* 1959; 14(4): 541-551.

Capek, J. M. and R. J. Roy. Noninvasive Measurement of Cardiac Output During Partial $CO_2$ Rebreathing. *IEEE Transactions on Biomedical Engineering.* 35: 653-61, 1988.

Capek, J. M. and R. J. Roy. Encyclopedia of Medical Devices and Instrumentation. J. G. Webster Ed. Wiley, N.Y. 1988. pp. 1309-10.

Defares J G. Determination of $P\bar{v}_{CO_2}$ From the exponential $CO_2$ Rise During Rebreathing. *J. Appl. Physiol.* 1958; 13(2): 159-64.

Gabrielsen A, Videbaek R, Schou M, Damgaard M, Kastrup J, Norsk P. Non-invasive measurement of cardiac output in heart failure patients using a new foreign gas rebreathing technique. *Clinical Science.* 2002; 102: 247-52.

Gedeon A, Forslund L, Hedenstierna G and Romano E. A new method for non-invasive bedside determination of pulmonary blood flow. *Med Biol Eng Comput.* 18: 411-8, 1980.

Hook C, Meyer M. Pulmonary blood flow, diffusing capacity and tissue volume by rebreathing: theory. *Respir. Physiol.* 1982; 48: 255-279.

Kelman, G. R. Digital computer subroutine for the conversion of oxygen tension into saturation. *J. Appl. Physiol.* 21(4): 1375-1376, 1966.

Kelman, G. R. Digital computer procedure for the conversion of $PCO_2$ into blood $CO_2$ content. *Respir. Physiol.* 3: 111-115, 1967.

Kim T S, Rahn H, Farhi L E. Estimation of true venous and arterial $PCO_2$ by gas analysis of a single breath. *J. Appl. Physiol.* 21(4): 1338-44, 1966.

Ljung, L. System Identification—Theory For the User 2e, PTR Prentice Hall, Upper Saddle River, N.J. 1999.

McDonnell W F and Seal E. Relationships between lung function and physical characteristics in young adult black and white males and females. *Eur respir J.* 4: 279-89, 1991.

Nunn J. Nunn's Applied Respiratory Physiology, 4th Edition, Butterworth-Heinemann, 1993, pp 196-7.

Orr et al. Method of continuously, non-invasively monitoring pulmonary capillary blood flow and cardiac output. U.S. Pat. No. 6,217,524 B1, 2001.

Petrini M F, Peterson B T, Hyde R W. Lung tissue volume and blood flow by rebreathing: theory. *J Appl. Physiol.* 44: 795-802, 1978.

Peyton P J, Robinson G J B, McCall P R and Thompson B. Non-invasive measurement of intrapulmonary shunting. *J Cardiothoracic Vasc Anesth.* 2004

Robinson G J B, Peyton P J, Vartuli G M, Burfoot R B, Junor P A. Continuous Measurement of Cardiac Output by Inert Gas Throughflow—Comparison with Thermodilution. *J. Cardiothorac. Vasc. Anesth.* 2003; 17(2):204-10.

Russell A E, Smith S A, West M J, Aylward P E, McRitchie R J, Hassam R M, Minson R B, Wing L M H and Chalmers J P. Automated non-invasive measurement of cardiac output by the carbon dioxide rebreathing method: comparisons with dye dilution and thermodilution. *Br. Heart J.* 63:195-9, 1990.

Sackner M A, Khalil A F and DuBois A B. Determination of tissue volume and carbon ioxide dissociation slope of the lungs in man. *J Appl Physiol.* 19(3): 374-80, 1964.

Sainsbury M C, Lorenzi A, Williams E M, Hahn C E W. A reconciliation of continuous and tidal ventilation gas exchange models, Resp Physiol 1997; 108: 89-99.

Siggaard-Andersen, O. The Acid-Base Status of the Blood, 4th edition. Copenhagen, Munksgaard Publishers. 1974, pp 51, 63.

Wessel H U, Stout R L, Bastanier C K and Paul M H. Breath-by breath variation of FRC: effect on $VO_2$ and $VCO_2$ measured at the mouth. *J. Appl. Physiol. Respirat. Environ. Exercise Physiol.* 46(6): 1122-6, 1979.

Yem J S, Tang Y, Turner M J and Baker A B. Sources of Error in Noninvasive Pulmonary Blood Flow Measurements by Partial Rebreathing. Anesthesiology 2003; 98:881-7.

The invention claimed is:

1. A method for monitoring cardiac output (pulmonary blood flow) of a subject, the method including:
   (i) making a first measurement of a gas species breathed by said subject at a first time to determine a first measurement value;
   (ii) determining a first pulmonary blood flow of said subject at said first time;
   (iii) making a second measurement of said gas species breathed by said subject at a second time later than said first time to determine a second measurement value; and
   (iv) determining a pulmonary blood flow of said subject at said second time on the basis of a product of said first pulmonary blood flow and a square of a ratio of the first measurement value and the second measurement value;
   wherein:
   (a) said first measurement value represents a net rate of pulmonary uptake or elimination of said gas species by said subject at said first time, and said second measurement value represents a net rate of pulmonary uptake or elimination of said gas species by said subject at said second time; or
   (b) said first measurement value represents a difference in partial pressures of said gas species between inspired and end-tidal gas at said first time, and said second measurement value represents a difference in partial pressures of said gas species between inspired and end-tidal gas at said second time; or
   (c) said first measurement value represents a partial pressure in end-tidal gas of said gas species at said first time, and said second measurement value represents a partial pressure in end-tidal gas of said gas species at said second time.

2. A method as claimed in claim 1, including:
   determining a first rate of change of partial pressure of said gas species in lungs of said subject at said first time; and
   determining a second rate of change of partial pressure of said gas species in lungs of said subject at said second time;
   wherein said pulmonary blood flow of said subject at said second time is determined on the basis of said first and second rates of change of partial pressure of said gas species in lungs of said subject at said first and second times.

3. A method according to claim 2, wherein $\dot{Q}t_k$, the pulmonary blood flow ($\dot{Q}t$) for a breath k ($\dot{Q}t_k$), is determined according to:

$$\dot{Q}t_k = \dot{Q}t_i \cdot \left(\frac{\dot{V}_{G_k}}{\dot{V}_{G_i}}\right)^2$$

where $\dot{V}_{G_i}$ and $\dot{V}_{G_k}$ are net rates of pulmonary uptake or elimination of a breathed gas species G for breath k and for an earlier breath i, respectively, and $\dot{Q}t_i$ is a pulmonary blood flow of said subject for said breath i.

4. A method according to claim 3, wherein the net rate of pulmonary uptake or elimination of said gas species G for each breath is approximated by a difference between an inspired partial pressure of said gas species G ($P_{I_G}$) and its partial pressure in end-tidal gas ($P_{E'_G}$) for a corresponding breath, so that said pulmonary blood flow $\dot{Q}t_k$ for a breath k of said subject is determined from $\dot{Q}t_i$, a pulmonary blood flow of said subject for an earlier breath i, according to:

$$\dot{Q}t_k = \dot{Q}t_i \left(\frac{P_{I_{G_k}} - P_{E'_{G_k}}}{P_{I_{G_i}} - P_{E'_{G_i}}}\right)^2.$$

5. A method according to claim 2, wherein $\dot{Q}t_k$, the pulmonary blood flow ($\dot{Q}t$) for a breath k ($\dot{Q}t_k$), is determined according to:

$$\dot{Q}t_k = \dot{Q}t_i \cdot \left(\frac{\dot{V}_{G_k}}{\dot{V}_{G_i}}\right)^2 \cdot \text{corr}$$

where $\dot{V}_{G_i}$ and $\dot{V}_{G_k}$ are net rates of pulmonary uptake or elimination of a breathed gas species G for said breath k and for an earlier breath i, respectively, $\dot{Q}t_i$ is a pulmonary blood flow of said subject for said breath i, and corr represents at least one correction factor to correct the measured value of at least one of $\dot{V}_{G_i}$ and $\dot{V}_{G_k}$.

6. A method according to claim 5, wherein said at least one correction factor corr includes a correction factor to correct for a change in metabolic rate due to a change in body temperature of said subject.

7. A method according to claim 5, wherein said at least one correction factor corr includes a correction factor to correct for a change in the level of alveolar ventilation of said subject.

8. A method as claimed in claim 1, including:
determining an effective lung volume of said subject at said first time;
wherein the pulmonary blood flow of said subject at said second time is determined on the basis of said effective lung volume.

9. A method according to claim 8, wherein $\dot{Q}t_k$, the pulmonary blood flow ($\dot{Q}t$) for a breath k ($\dot{Q}t_k$), is determined according to:

$$\dot{Q}t_k = \dot{Q}t_i \left(\frac{P_{I_{G_k}} - P_{E'_{G_k}}}{P_{I_{G_i}} - P_{E'_{G_i}}}\right)^2$$

where $P_{I_{G_k}}$ represents an inspired partial pressure of said gas species G for said breath k and $P_{E'_{G_k}}$ represents its partial pressure in end-tidal gas for said breath k, $P_{I_{G_i}}$ represents an inspired partial pressure of said gas species G for an earlier breath i and $P_{E'_{G_i}}$ represents its partial pressure in end-tidal gas for said earlier breath i, and $\dot{Q}t_i$ represents the pulmonary blood flow ($\dot{Q}t$) for said earlier breath i.

10. A method according to claim 1, wherein the pulmonary blood flow of said subject is determined for each of a plurality of second times later than said first time and corresponding to successive breaths of said subject to provide breath-by-breath determination of said pulmonary blood flow of said subject.

11. A method according to claim 10, wherein $\dot{Q}t_k$, the pulmonary blood flow ($\dot{Q}t$) for a breath k ($\dot{Q}t_k$), is determined according to:

$$\dot{Q}t_k = \dot{Q}t_i \left(\frac{P_{E'_{G_k}}}{P_{E'_{G_i}}}\right)^2$$

wherein $\dot{Q}t_k$ is the pulmonary blood flow ($\dot{Q}t$) for a breath k, $P_{E_{G_k}}$ represents a partial pressure in end-tidal gas of an inspired gas species G for said breath k, $P_{E'_{G_i}}$ represents its partial pressure in end-tidal gas for an earlier breath i, and $\dot{Q}t_i$ represents the pulmonary blood flow ($\dot{Q}t$) for said earlier breath i.

12. A method according to claim 1 wherein the gas species is carbon dioxide ($CO_2$).

13. A method according to claim 1, wherein the subject is human.

14. A system for monitoring cardiac output (pulmonary blood flow) of a subject, the system including at least one processor and at least one non-transitory processor-readable storage medium communicatively coupled to the at least one processor, the system configured to perform the method of claim 1.

15. A non-transitory computer-readable storage medium having stored therein programming instructions for performing the method of claim 1.

16. The method according to claim 1, wherein said first measurement value represents said net rate of pulmonary uptake or elimination of said gas species by said subject at said first time, and said second measurement value represents said net rate of pulmonary uptake or elimination of said gas species by said subject at said second time.

17. The method according to claim 1, wherein said first measurement value represents said difference in partial pressures of said gas species between inspired and end-tidal gas at said first time, and said second measurement value represents said difference in partial pressures of said gas species between inspired and end-tidal gas at said second time.

18. The method according to claim 17, wherein the partial pressure of said gas species in inspired gas at said first time and the partial pressure of said gas species in inspired gas at said second time are or are assumed to be negligible, so that the pulmonary blood flow of said subject at said second time is determined on the basis of a product of said first pulmonary blood flow and a square of a ratio of the partial pressure of said gas species in end-tidal gas at said first time and the partial pressure of said gas species in end-tidal gas at said second time.

19. A system for monitoring cardiac output (pulmonary blood flow) of a subject, the system including:
(i) means for making a first measurement of a gas species breathed by said subject at a first time to determine a first measurement value;
(ii) means for determining a first pulmonary blood flow of said subject at said first time;
(iii) means for making a second measurement of said gas species breathed by said subject at a second time later than said first time to determine a second measurement value; and
(iv) means for determining a pulmonary blood flow of said subject at said second time on the basis of a product of said first pulmonary blood flow and a square of a ratio of the first measurement value and the second measurement value;
wherein:
(a) said first measurement value represents a net rate of pulmonary uptake or elimination of said gas species by said subject at said first time, and said second measurement value represents a net rate of pulmonary uptake or elimination of said gas species by said subject at said second time; or
(b) said first measurement value represents a difference in partial pressures of said gas species between inspired and end-tidal gas at said first time, and said second measurement value represents a difference in partial pressures of said gas species between inspired and end-tidal gas at said second time.

20. A system according to claim 19, including:
a gas analyzer for measuring partial pressures of said gas species inhaled and/or exhaled by said subject; and a gas flow or volume measurement device for measuring flow of said gas species inhaled and/or exhaled by said subject, and further including means for determining alveolar partial pressures at said first and second times and net rates of uptake or elimination by the lungs of said gas species at said first and second times.

21. A system according to claim 19, including means for performing one or more data averaging or smoothing operations to determine the pulmonary blood flow of the subject.

22. A system according to claim 19, wherein the system is operable to determine the pulmonary blood flow of said subject for each of a plurality of second times later than said first time and corresponding to successive breaths of said subject to provide breath-by-breath determination of said pulmonary blood flow of said subject.

23. A non-transitory computer-readable storage medium having stored therein programming instructions for performing the steps of:
(i) accessing first measurement data representing a first measurement of a gas species breathed by a subject at a first time;
(ii) determining a first pulmonary blood flow of said subject at said first time;
(iii) accessing second measurement data representing a second measurement of said gas species breathed by said subject at a second time later than said first time; and
(iv) processing said first measurement data and said second measurement data to determine a pulmonary blood flow of said subject at said second time on the basis of a product of said first pulmonary blood flow and a square of a ratio of said first measurement data and the second measurement data;
wherein:
(a) said first measurement data represents a net rate of pulmonary uptake or elimination of said gas species by said subject at said first time, and said second measurement data represents a net rate of pulmonary uptake or elimination of said gas species by said subject at said second time; or
(b) said first measurement data represents a difference in partial pressures of said gas species between inspired and end-tidal gas at said first time, and said second measurement data represents a difference in partial pressures of said gas species between inspired and end-tidal gas at said second time.

\* \* \* \* \*